(12) United States Patent
Yoneyama et al.

(10) Patent No.: US 7,346,145 B2
(45) Date of Patent: Mar. 18, 2008

(54) X-RAY IMAGING SYSTEM

(75) Inventors: Akio Yoneyama, Kawagoe (JP); Yasuharu Hirai, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 125 days.

(21) Appl. No.: 11/340,526

(22) Filed: Jan. 27, 2006

(65) Prior Publication Data
US 2006/0256918 A1    Nov. 16, 2006

(30) Foreign Application Priority Data
May 13, 2005    (JP) .............................. 2005-140746

(51) Int. Cl.
*G01T 1/36* (2006.01)

(52) U.S. Cl. .......................................... 378/82; 378/84

(58) Field of Classification Search .................. 378/82, 378/84
See application file for complete search history.

(56) References Cited

U.S. PATENT DOCUMENTS

| | | | | |
|---|---|---|---|---|
| 3,446,961 A | * | 5/1969 | Ulrich et al. .................. | 378/36 |
| 5,173,928 A | * | 12/1992 | Momose et al. ................ | 378/4 |
| 5,259,013 A | * | 11/1993 | Kuriyama et al. ............. | 378/43 |
| 5,715,291 A | * | 2/1998 | Momose ....................... | 378/84 |
| 5,802,137 A | * | 9/1998 | Wilkins ........................ | 378/85 |
| 5,812,629 A | * | 9/1998 | Clauser ........................ | 378/62 |
| 5,850,425 A | * | 12/1998 | Wilkins ........................ | 378/85 |
| 5,864,599 A | * | 1/1999 | Cowan et al. ................ | 378/43 |
| 6,577,708 B2 | * | 6/2003 | Chapman et al. ............. | 378/82 |
| 6,870,896 B2 | * | 3/2005 | Protopopov ................... | 378/36 |
| 7,076,025 B2 | * | 7/2006 | Hasnah et al. ................ | 378/82 |
| 7,113,564 B2 | * | 9/2006 | Yoneyama ..................... | 378/36 |
| 7,180,979 B2 | * | 2/2007 | Momose ....................... | 378/62 |

FOREIGN PATENT DOCUMENTS

| | | |
|---|---|---|
| JP | 04-348262 | 7/1991 |
| JP | 09-187455 | 1/1996 |
| JP | 10-248833 | 3/1997 |
| WO | WO 95-05725 | 8/1994 |

\* cited by examiner

*Primary Examiner*—Edward J. Glick
*Assistant Examiner*—Thomas R. Artman
(74) *Attorney, Agent, or Firm*—Reed Smith LLP; Stanley P. Fisher, Esq.; Juan Carlos A. Marquez, Esq.

(57) ABSTRACT

To obtain an image that uses both an accurate spatial differential of an object-caused phase shift and the phase shift as contrast at a small observation field of view and under a simplified apparatus configuration , , , .

a spatial differential of the object-caused phase shift and the phase shift are arithmetically obtained from the diffraction images of the object formed by simultaneous X-ray diffraction of crystals.

19 Claims, 18 Drawing Sheets

DIFFRACTION REGION

| FIG.3A | FIG.3B | FIG.3C |
|---|---|---|
| ORIGINAL SAMPLE IMAGE | DIFFRACTION IMAGE BY ANALYZER CRYSTAL | PHASE-CONTRAST IMAGE BY ROTATING CRYSTAL METHOD |
| 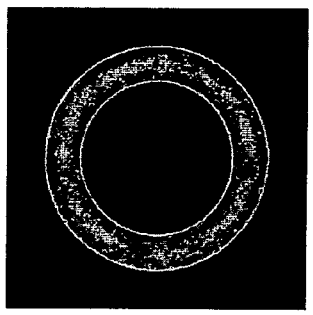 | 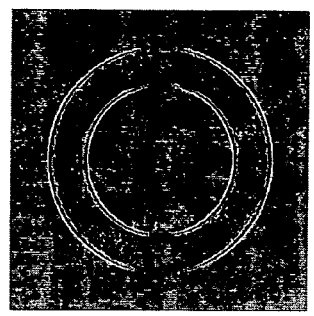 | 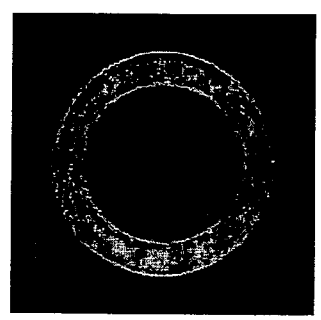 |
| 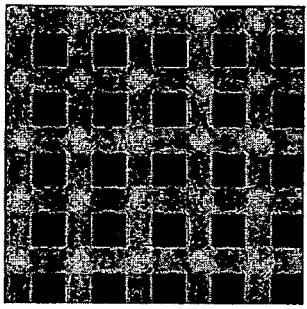 | 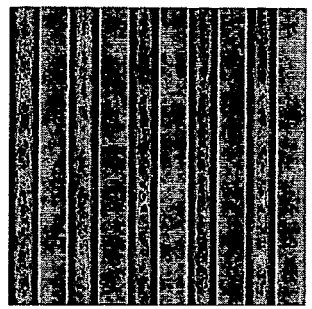 | 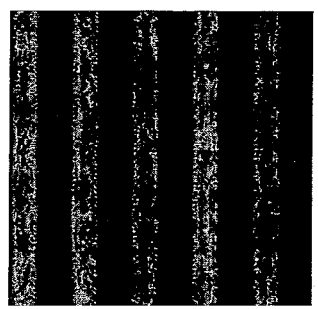 |

FIG.6A
FIG.6B
FIG.6C
DIFFRACTION IMAGE OBTAINED BY (n11)
DIFFRACTION IMAGE OBTAINED BY ($n\bar{1}\bar{1}$)
DIFFRACTION IMAGE OBTAINED BY USING THIS INVENTION
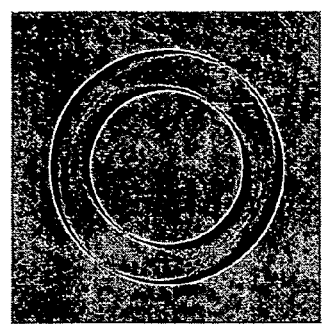
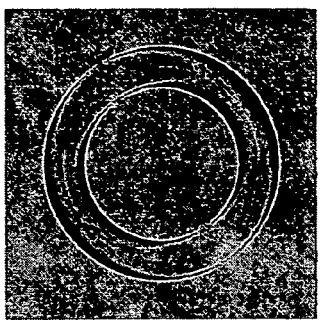
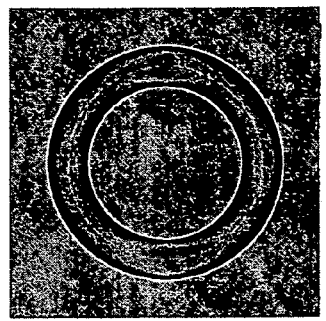
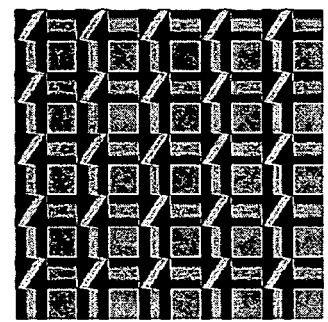
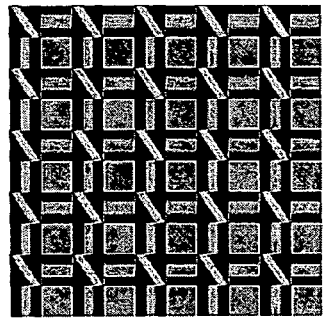
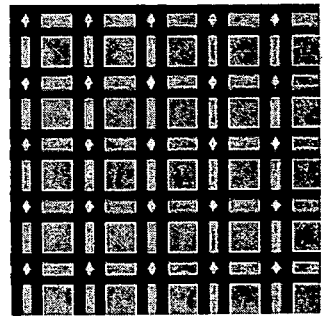

FIG.9
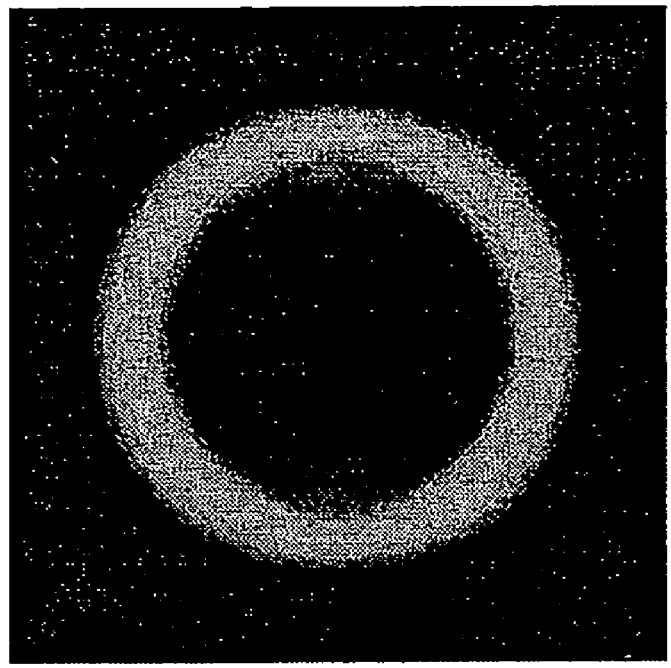
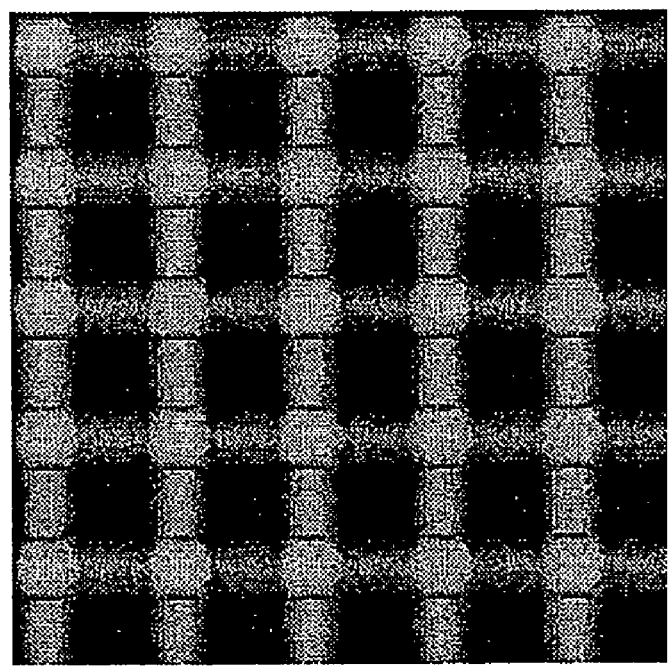

X-RAY IMAGING SYSTEM

CLAIM OF PRIORITY

The present application claims priority from Japanese application JP 2005-140746, filed on May 13, 2005, the content of which is hereby incorporated by reference into this application.

FIELD OF THE INVENTION

The present invention relates to an X-ray imaging system, the system being adapted for nondestructive observation and inspection of a body interior.

BACKGROUND OF THE INVENTION

X-ray imaging systems are intended to observe the inside of an irradiation target body two-dimensionally or three-dimensionally nondestructively by utilizing the high transmissibility of X-rays with respect to the body. The internal density of a body that is a basic physical quantity is used as contrast for such a system to form images. Methods of detecting the density can be broadly divided into two types. One type is used to obtain the density from a change in X-ray intensity, caused by absorption when the X-rays transmit the target body, and the other type is used to obtain the density from a phase shift caused during the transmission. The former type is called "absorption contrast X-ray imaging", and the latter type, "phase contrast X-ray imaging".

The imaging systems using the former detection method, namely, absorption contrast X-ray imaging systems, are each composed mainly of an X-ray source, a target body holder, and a detector. In these systems, the target body positioned using the target body holder is irradiated with the X-rays emitted from the X-ray source, then the intensity of the X-rays transmitting the body is detected by the detector, and images are formed. The configuration of these systems are simple in terms of measuring principles. Therefore, these systems are commonly used in many fields, including medical diagnosis, under the name of roentgen systems for two-dimensional observation, and X-ray CT systems for three-dimensional observation by CT (Computed Tomography). However, since hydrogen, carbon, oxygen, and other light elements are almost transparent to X-rays and essentially do not change X-ray intensity, the above systems are low in sensitivity with respect to the biological soft tissues, organic materials, and other target bodies constructed mainly of light elements. To apply such a system, therefore, it is necessary to perform operations such as using the contrast agents that contain a heavy metal(s), or extending an exposure time.

The imaging systems using the latter detection method, namely, phase contrast X-ray imaging systems, require the means that detects phase shifts, in addition to the above system components. Compared with absorption contrast X-ray imaging systems, however, phase contrast X-ray imaging systems are very high in sensitivity and enable observations of biological soft tissues without contrast agents and without harmful levels of X-ray exposure. These advantages are due to the fact that the phase-shift cross-section are about 1,000 times as great in light elements as the absorption cross-section. Examples of phase-shift detection means include as described in Phys. Today 53 (2000) 23: (1) the methods that use an X-ray interferometer described in Japanese Laid-Open Patent Application Publication Nos. Hei 4-348262 and Hei 10-248833, (2) the methods that use an analyzer crystal to detect diffracted X-ray angles described in International Patent Application Laid-Open Publication No. WO95/05725—Pamphlet and in Japanese Laid-Open Patent Application Publication No. Hei 9-187455, and (3) a method that uses Fresnel diffraction.

Table 1 lists comparison results on the physical quantities detected using each of the above-mentioned methods, and on the respective sensitivities, dynamic ranges, spatial resolution levels, and other features and characteristics.

TABLE 1

|  | (1) Method using an X-ray interferometer | (2) Method using an analyzer crystal | (3) Method using Fresnel diffraction |
| --- | --- | --- | --- |
| Detection principles | Using an X-ray interferometer to cause interference between a material wave and a reference wave, and then detect phase shifts from the resulting interference fringes | Using Bragg diffraction of a crystal to detect the angle of object-diffracted X-rays (Using the crystal as an angle analyzer) | Detecting the Fresnel fringes caused by Fresnel diffraction |
| Physical quantity detected | cos p (p: density) | ∂p/∂x | $\nabla^2 P$ |
| Relative sensitivity | ◉ | ○ | Δ |
| Dynamic range | Δ | ○ | ○ |
| Spatial resolution | 10 microns | Several microns | Several microns |
| Others | Unwrapping required. | Sensitivity is in a one-dimensional direction only. | A third generation of synchrotron radiation or the like is required. |

It can be seen from the above table that the method using an analyzer crystal is best balanced with respect to each item. This method has features in that it, compared with the method using an X-ray interferometer, is relatively simple in system configuration, and in that it, unlike the method that uses Fresnel diffraction, does not require a special light source.

A method using an analyzer crystal, concerned with the present invention, will be described hereunder.

When X-rays transmit an object that causes a phase shift φ, if the phase shift φ is spatially nonuniform, a propagating direction of the X-rays will be bent through an angle of θ by diffraction. The angle θ is given as a function of a spatial differential (dφ/dx) of φ, by expression (1).

(Numerical expression 1)

$$\theta = \frac{\lambda}{2\pi} \frac{d\phi}{dx} \qquad (1)$$

A spatial differential of the phase shift can therefore be calculated by detected θ. In addition, the phase can be calculated by spatially integrating θ.

For the method described in International Patent Application Laid-Open Publication No. WO95/05725—Pamphlet, Bragg diffraction of the monolithic crystal in the shape of a flat plate, called the analyzer crystal, is utilized to detect θ, that is, the spatial differential of the phase shift. Bragg diffraction is a phenomenon in which, when the wavelength of an incident X-ray is defined as "λ", and the lattice spacing of its diffraction plane as "d", the incident X-ray will be diffracted by the analyzer crystal only if the incident angle $\theta_b$ of the X-ray satisfies the diffraction condition shown in expression (2) below, within an angle range of several seconds.

$$\lambda = 2d \sin\theta_b \qquad (2)$$

(Numerical Expression 2)

Therefore, if $\theta_b$ is set so as to satisfy expression (2) when a deflection angle $\theta$ of the X-ray in the propagating direction thereof is equal to 0, intensity I of the X-ray diffracted will depend on $\theta$, become a maximum when $\theta=0$, and decrease as increasing of $\theta$. When $\theta$ is several seconds of angle, therefore, intensity I of the X-ray will almost equal 0. This phenomenon is utilized to obtain an image of the spatial differential of the phase shift from a spatial distribution of the X-ray's intensity I (i.e., a diffracted image).

Since diffraction intensity I of X-rays is almost constant at $\theta b \pm \theta$, measurement of I is only useful for determining the magnitude of $\theta$ and provides no information on the direction thereof. The integral of $\theta$, therefore, cannot be calculated, and the phase shift itself cannot be calculated, either. For these reasons, as described in Japanese Laid-Open Patent Application Publication No. Hei 9-187455, the magnitude and direction of $\theta$ are detected from the diffraction intensity I that has been acquired at various angles by rotating the analyzer crystal, and then the phase shift is calculated by integration. After this, sectional images of the object are obtained by computed tomography using the phase shift as contrast in combination with the rotation of the sample.

SUMMARY OF THE INVENTION

Considerations will be conducted on an example in which, as shown in FIG. 1, an X-ray 100 that has been irradiated into a target object 101 is refracted by the object, bended two-dimensionally, and incidented upon an analyzer crystal 102 bent. Assume that when the object 101 is absent, the incident X-ray 100 is, as denoted by a broken line, is irradiated towards the origins of the x-, y-, and z-axes, each denoted by a broken line, then reaches the surface of the analyzer crystal 102 at an incident angle $\theta_b$ with respect to the z-axis, along an x-z plane, and is diffracted as a diffracted X-ray 103. When the object 101 is installed, the incident X-ray 100 is refracted by the object 101 and bent to follow a path 104. The x-axis component of the angle $\theta$ formed by the incident X-ray 100 without bent and the path 104, that is, the deflection $\theta_x$ of the incident angle in a plane formed by the incident X-ray 100 and the diffracted X-ray 103 (x-z plane) becomes the deflection $\Delta\theta_b$ itself of the incident angle $\theta_b$ in expression (2). Since the Bragg's condition of diffraction in expression (2) is applied intact, therefore, intensity I of the diffracted X-ray sensitively changes with respect to $\theta_x$.

In contrast to the above, the y-axis component of the angle $\theta$ formed by the rectilinear incident X-ray 100 and the path 104, that is, the deflection $d\rho$ of the incident angle in a plane vertical to the plane formed by the incident X-ray and the diffracted X-ray (y-z plane), has the relationship with the deflection $\Delta\theta_b$ of $\theta_b$ that is shown in expression (3).

$$\Delta\theta_b = \tan\theta_b (1 - \cos d\rho) \qquad (3)$$

(Numerical Expression 3)

Since the susceptibility of $\Delta\theta_b$ to $d\rho$ is very low, intensity of the diffracted X-ray essentially does not change.

FIG. 2 is an epitomic representation of the region in which X-ray diffraction occurs against $\theta_x$ and $d\rho$. This figure indicates that at narrower sections of the region, diffraction intensity changes more sensitively, namely, angular resolution becomes higher, with respect to an angular deflection. It can therefore be seen that there is almost no angular resolution with respect to $d\rho$ and thus that there is the problem that the spatial differential of the phase shift in the y-axis direction cannot be obtained.

Spatial distribution images (diffraction images) of the diffraction intensity I which was calculated from numerical simulation results on the donut-shaped and mesh-shaped target objects shown in FIG. 3A are shown in FIG. 3B by way of example. FIG. 3B indicates that since the intensity of diffracted light does not almost change against $d\rho$, the contrast of the images is lost in the y-axis direction.

In Japanese Laid-Open Patent Application Publication No. Hei 9-187455, the absence of angular resolution with respect to $d\rho$ also poses a problem during integral calculation of $\theta x$ for the determination of the phase shift. During the integral calculation, the initial phase value of its starting point needs to be known. However, the absence of angular resolution in the y-axis direction makes it absolutely necessary for the above initial value to be set in the external background region of the object that is already known to be zero. The initial value must be set in the background region before accurate images can be obtained. Phase-contrast images each with contrast based on the phase shift that was arithmetically determined using the method described in Japanese Laid-Open Patent Application Publication No. Hei 9-187455 are shown in FIG. 3C. For the donut-shaped object, the obtained image of its original shape shown in 3A exhibits high reproducibility since integral calculation can be started from the background. For the mesh-shaped object, however, since the absence of a background makes initial value setting impossible, a y-axial phase shift cannot be detected and the obtained image is not reproduced well. These results indicate that the method concerned has a problem in that it absolutely requires a wide observation field in which the entire target object can be observed.

An object of the present invention is to provide means that makes it possible to detect a spatial differential of a phase shift caused by a target object, and to detect the phase shift, without observing the entire object.

The present invention solves the above problems by using simultaneous diffraction as the X-ray diffraction using an analyzer crystal. The simultaneous diffraction here refers to a phenomenon in which an X-ray beam incident on the crystal simultaneously satisfies the diffraction conditions of plural crystal lattice planes and the beam is split into a plurality of beams by diffraction from each lattice plane. Similarly to normal X-ray diffraction, a Bragg-case and a Laue-case are present and both are further broadly divided into a coplanar type in which the planes formed by the incident X-ray beam and each diffracted X-ray beam are all parallel, and a nonplanar type in which the planes formed are not parallel. The present invention employs nonplanar simultaneous diffraction based on the Bragg-case and the Laue-case.

The Bragg-case nonplanar simultaneous diffraction using an (n11) plane and an (n−1−1) plane, as shown in FIG. 4, will be described hereunder. The description assumes that a lattice plane parallel to a crystal surface is defined as an (m00) plane and that a [011] plane is parallel to an x-z plane.

When the angle formed by the (m00) plane and the [n11] plane is taken as $\theta a$, and the angle formed by the (m00) plane and an x-y plane, as θb, unit vector "n" of diffraction lattice vectors is represented by expression (4).

$$n=(-\cos\theta_a \sin\theta_b, -\sin\theta_a, \cos\theta_a \cos\theta_b) \quad (4)$$

(Numerical Expression 4)

where the (n−1−1) plane means the (n11) plane. The same also applies throughout the remainder of this Specification.

When an X-ray of a wave number vector "ko" enters an analyzer crystal 102 as shown in FIG. 4, unit vector "a" of "ko" is given by expression (5) with the deflection from the x-z plane as dρ.

It follows from expressions (4) and (5) that incident angle $\theta_i$ of "ko" with respect to the (n11) plane is given by expression (6).

$$a=(\cos d\rho, -\sin d\rho, 0) \quad (5)$$

$$\theta_i = \sin^{-1}(-\cos\theta_a \sin\theta_b \cos d\rho + \sin\theta_a \sin d\rho) \quad (6)$$

(Numerical Expression 6)

Also, incident angle $\theta_i$, with respect to the (n−1−1) plane is given by expression (7).

$$\theta_i = \sin^{-1}(-\cos\theta_a \sin\theta_b \cos d\rho - \sin\theta_a \sin d\rho) \quad (7)$$

(Numerical Expression 7)

Hence, when dρ=0, $\theta_i = \theta_i$, and if the wavelength λ of the incident X-ray satisfies the diffraction condition shown in expression (8), the incident X-ray is diffracted by both the (n11) and (n−1−1) planes at the same time (simultaneous diffraction) and consequently split into an X-ray of a wave number $k_h$ and an X-ray of $k_{h'}$.

$$\lambda = 2d \sin\theta_i \quad (8)$$

(Numerical Expression 8)

Where "d" is a lattice plane spacing of the (n11) and (n−1−1) planes.

FIG. 5 shows regions in which, as in FIG. 2, X-ray diffraction with respect to both the deflection $\theta_x$ and dρ occurs on the above (n11) and (n−1−1) planes. Individual diffraction on each lattice plane is the same phenomenon as normal Bragg diffraction, and since the X-ray enters obliquely with respect to the lattice planes, the diffraction regions are merely inclined in comparison with the region of FIG. 2. This inclination, $\theta_s$, is given by expression (9).

$$\theta_s = \tan^{-1}(\cos\theta_b / \tan\theta_a) \quad (9)$$

(Numerical Expression 9)

When the diffraction region by the (n11) plane in FIG. 5 is taken as A and the diffraction region by the (n−1−1) plane as B, a region in which both of the two regions overlap on each other to cause simultaneous diffraction is given as C in expression (10), it can be seen that C is confined to a very narrow central section at which $\theta_x$ and dρ become almost zero.

$$C = A \cap B \quad (10)$$

(Numerical Expression 10)

The diffraction using the region C as a diffraction region, diffraction intensity sensitively changes with respect to both $\theta_x$ and dρ. Therefore, a calculation of "virtual diffraction intensity Ii obtained in diffraction region C" from the diffraction intensity of the simultaneous diffraction on the (n11) and (n−1−1) planes, makes it possible to obtain an image in which a spatial differential of a phase shift sensitive to both $\theta_x$ and dρ is taken as contrast.

More specifically, the "virtual diffraction intensity $I_i$ obtained in diffraction region C" is calculated as follows. That is, if the X-ray deflection θ caused by refraction during passage through the object is present at point P in FIG. 5, since point P is included in the diffraction region A of the (n11) plane, the incident X-ray is diffracted on the (n11) plane. Conversely, point P is present outside the diffraction region B of the (n−1−1) plane, the incident X-ray is not diffracted on the (n−1−1) plane. In addition, during the virtual diffraction that uses C as its diffraction region, since point P is present outside C, the X-ray is not diffracted as can be seen from FIG. 5. This indicates that under this condition, diffraction intensity by the (n−1−1) plane can be adopted as intensity of the virtual diffraction whose diffraction region is given as C. Conversely, at point P' that is included in the region B but not included in the region A, since the inverse of the above applies, diffraction intensity by the (n11) plane can be adopted as $I_i$. These facts mean that the "virtual diffraction intensity $I_i$ obtained in diffraction region C" can be calculated using expression (11).

$$Ii = \min(I_1, I_2) \quad (11)$$

(Numerical Expression 11)

In the above expression, $I_1$ is the diffraction intensity by the (n11) plane, $I_2$ is the diffraction intensity by the (n−1−1) plane, and min(a, b) is a function that returns a value of "a" or "b", whichever is the smaller.

The (n11) plane and (n−1−1) plane diffraction images that were obtained from numerical simulation results on the objects shown in FIG. 3A, and the "virtual diffraction intensity $I_i$ obtained in diffraction region C" that was calculated from both images by expression (11) are shown in FIGS. 6A to 6C. These calculation results indicate that the (n11) plane and (n−1−1) plane diffraction images have their contrast lost in the directions of $\theta_s$ and $-\theta_s$. The loss is due to the fact that the intensity of the diffracted light does not change with respect to the refraction of the X-ray in those directions. Conversely, it can be seen that the contrast of the image with the "virtual diffraction intensity $I_i$ obtained in diffraction region C" is reproduced clearly in all directions without being lost.

With the above-described methods, since the intensity I of the diffracted X-ray takes essentially the same value at θb±θ, although the magnitude of θ can be determined, the direction thereof cannot be identified. This makes integral calculation impossible, thus making the phase shift itself undeterminable. To solve this problem, a method of detecting the magnitude and direction of θ from the diffraction intensity acquired for each angle after rotating an analyzer crystal 102 will be described next.

When the analyzer crystal 102 is rotated around the y-axis shown in FIG. 4, point P in FIG. 5 virtually moves in the horizontal direction indicated by the arrow in the figure. Diffraction intensity levels obtained on the (n11) and (n−1−1) planes, therefore, exhibit such profiles as in FIG. 7, with respect to the rotation of the analyzer crystal 102. If the analyzer crystal angles that maximize the intensity levels are taken as $\theta_1$ and $\theta_2$, $\theta_x$ is given as a central value between $\theta_1$ and $\theta_2$, from geometrical calculation, that is, by expression (12).

(Numerical expression 12)

$$\theta x = \frac{\theta_1 + \theta_2}{2} \quad (12)$$

(Numerical expression 13)

$$d\rho = \frac{\theta_1 - \theta_2}{2} \cdot \tan(\theta s) \quad (13)$$

In the above expression, $\theta_s$ is an angle given by expression (9). Hence, the magnitude of X-ray beam deflection $\theta$ caused by the object is given by expression (14), and the direction $\phi$ of the deflection can be calculated from expression (15).

(Numerical expression 14)

$$|\theta| = \sqrt{\theta_x^2 + d\rho^2} \qquad (14)$$
$$= \sqrt{(\theta_1 + \theta_2)^2/4 + (\theta_1 - \theta_2)^2 \tan^2\theta_s/4}$$

(Numerical expression 15)

$$\phi = \tan^{-1}(d\rho/\theta_x) \qquad (15)$$
$$= \tan^{-1}\left(\frac{\theta_1 - \theta_2}{\theta_1 + \theta_2}\tan\theta_s\right)$$

Additionally, as shown in FIG. 8, the phase shift can be calculated in three steps: (1) determining an initial phase value appropriately at a given point (say, an upper-left point) on the image, (2) calculating the amount of y-axial phase shift by integrating $d\rho$ one line from that point, and (3) integrating each $\theta_x$ component from the line at which the amount of phase shift was calculated in step (2) above.

FIG. 9 shows, in comparison with the numerical simulation results of FIGS. 3 and 6, the calculation results on phase-contrast images (images with a phase shift as its contrast) that were obtained by the measurement using the above-described method of rotating the analyzer crystal 102. It can be seen from these results that the object shape that was initially assumed in FIG. 3A is restored very well.

Sectional images of an object by nondestructive imaging which utilizes the high transmissibility of X-rays can be reconstructed in two steps: (1) with the object rotated with respect to an X-ray beam, acquiring phase-contrast images at various angles using the method described above, and (2) after completing all necessary measurements, reconstructing sectional images with the acquired phase-contrast images by calculation with a conventional X-ray CT algorithm.

Thus, an image that uses both a spatial differential of an object-caused phase shift and the phase shift as its contrast, can be detected without observing the entire object by using simultaneous diffraction as X-ray diffraction due to use of an analyzer crystal 102. In addition, a sectional image of the object with a phase shift as contrast can likewise be obtained by rotating the object.

According to the present invention, an image that uses, as its contrast, both an accurate spatial differential of an object-caused phase shift and the phase shift, can be obtained at a small observation field size and under a simplified apparatus configuration.

BRIEF DESCRIPTION OF THE DRAWINGS

FIG. 3 is a diagram that shows diffraction images based on numerical simulation, and phase-contrast images;

FIG. 6 is a diagram that shows diffraction images formed by simultaneous diffraction based on numerical simulation;

FIG. 9 is a diagram that shows phase-contrast images obtained in the present invention by numerical simulation;

DETAILED DESCRIPTION OF THE PREFERRED EMBODIMENTS

Embodiments of the present invention will be described hereunder using the accompanying drawings. In the figures shown below, the same reference number or symbol is assigned to sections having the same function, and duplicate description is omitted.

First Embodiment

Figure 10:
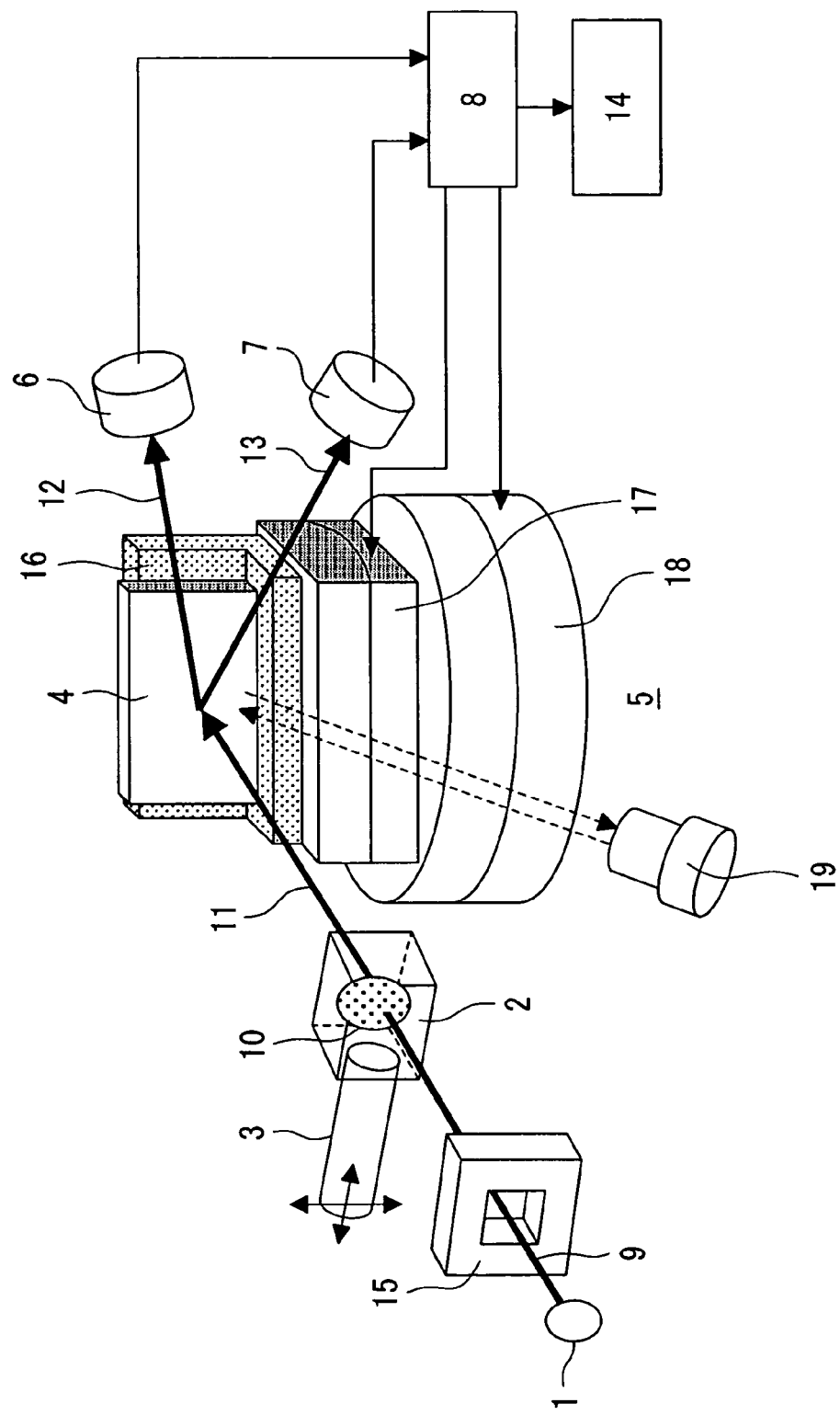
FIG. 10 is a diagram showing an embodiment of the present invention.

FIG. 10 is a block diagram showing an example of an X-ray imaging system according to the present invention. As shown in the figure, this system includes an X-ray source 1, a target object holder 2, an object holder supporting/positioning unit 3, an analyzer crystal 4, an analyzer crystal angle-adjusting unit 5, image detectors 6 and 7, and a processor 8.

A target object 10 inside the object holder 2 that has been positioned by the object holder supporting/positioning unit 3 is irradiated with an X-ray beam 9 emitted from the X-ray source 1. An X-ray beam 11 that has been refracted by the object after transmitting therethrough enters the analyzer crystal 4, and only components that satisfy the Bragg's condition of diffraction are diffracted to form diffracted X-ray beams 12 and 13. The diffracted X-ray beams 12 and 13 have respective intensity levels detected by image detectors 6 and 7, and pixel-by-pixel intensity levels are saved as image data in the processor 8. After this, "virtual diffraction intensity $I_i$ obtained in diffraction region C" is calculated from the saved image data in accordance with expression (11), and an image with $I_i$ as contrast, namely, an image with a spatial differential of a phase shift as contrast, is displayed at a display unit 14.

The X-ray source 1 may be of a normal tube type or a rotary type, or may be synchrotron radiation. In the former case, however, since the X-ray beam emitted is divergent light, background noise of the image detectors 6, 7 and exposure of the object 10 by scattered X-rays can be reduced when a slit 15 with a variable aperture width is placed between the X-ray source and the object.

The analyzer crystal 4 can be a crystal plate (or the like) formed by grinding a monolithic crystal and then polishing its surface into a non-strained state by mechano-chemical polishing or the like. The crystal has its dimensions determined considering an X-ray beam size extracted by the slit 15, wavelength of the X-ray beam, and the diffraction lattice plane sizes used. A horizontal size (width: W) of the X-ray beam 11 on the analyzer crystal 4 is given by expression (16), where a width of the X-ray beam 11 is taken as $W_b$, the wavelength is taken as $\lambda$, and the diffraction lattice planes used for simultaneous diffraction are taken as an (n11) plane and an (n-1-1) plane.

(Numerical expression 16)

$$W = \frac{2d\cos\theta_a}{\lambda} W_b \qquad (16)$$

Therefore, the analyzer crystal can have a width equal to or greater than W. In the above expression, "d" is a lattice spacing of the (n11) plane, and $\theta_a$ is an angle formed by the (n11) plane and the crystal surface. Meanwhile, since a vertical size (height: H) of the X-ray beam 11 on the analyzer crystal 4 is almost the same as a vertical size (height: $H_b$) of the X-ray beam 11 at other positions, the analyzer crystal 4 can have a vertical size equal to or greater than $H_b$.

The diffraction lattice planes that can be used for simultaneous diffraction exist in uncountable numbers. Lattice planes are therefore selected in the following procedure:

(1) Measuring a size (thickness) of the object 10 to be observed, (2) calculating an optimum X-ray energy level (wavelength) for the thickness of the object, and (3) selecting lattice planes whose $\theta_s$ is close to 45 degrees, whose $\theta_t$ is great (at least 10 degrees), and whose Miller index is as low as possible.

A thicker object 10 requires a higher X-ray energy level for increased transmissibility. As shown in expression (1), however, an angle of refraction $\theta$ by the object is proportional to $\lambda$, that is, inversely proportional to energy, so a higher energy level lessens the refractive angle $\theta$ and thus reduces phase-shift detection sensitivity.

Figure 11:
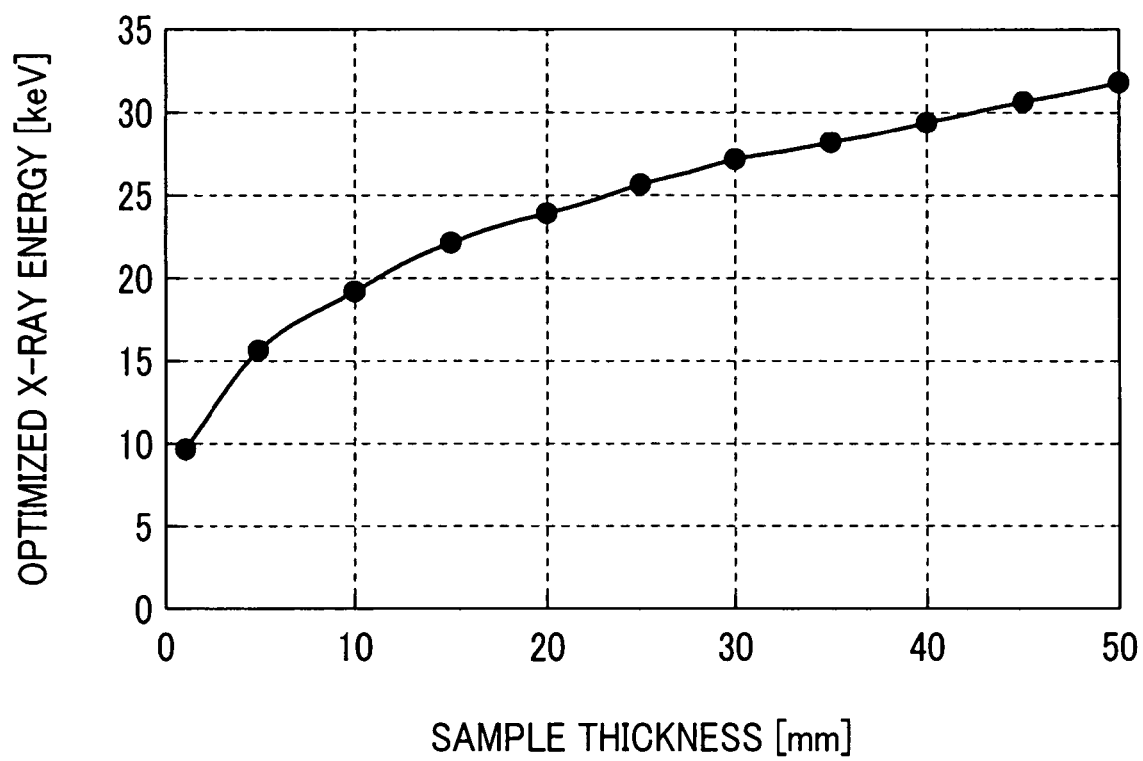
FIG. 11 is a diagram that shows optimum X-ray energy for thicknesses of objects.

In step (2) above, therefore, energy is determined using a graph that lists energy levels at which an S/N ratio of a typical object becomes a maximum for the thickness of the object. A graph of biological soft tissues is shown as an example in FIG. 11.

Figure 12:
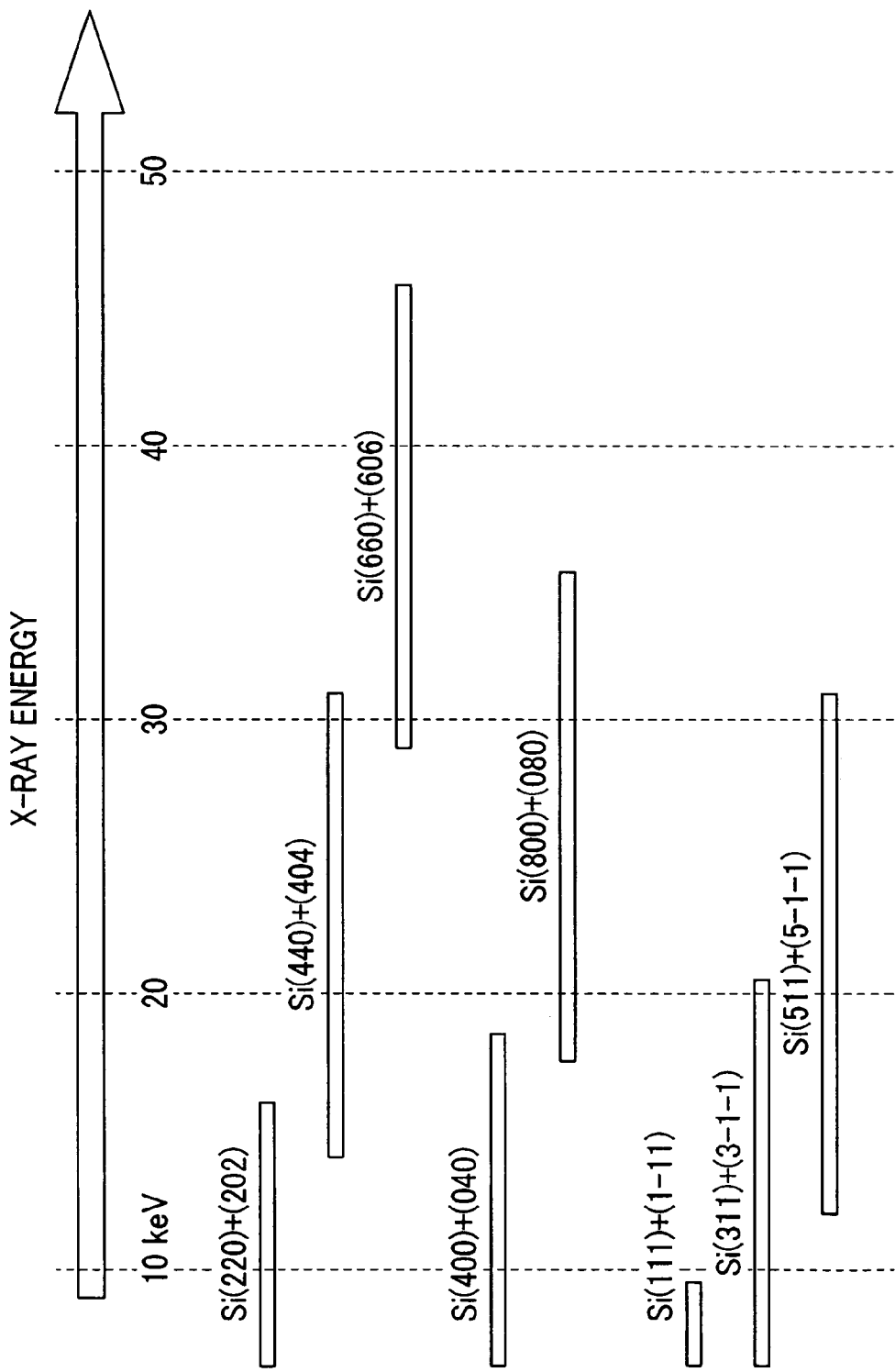
FIG. 12 is a diagram that shows optimum simultaneous diffraction plane with respect to each X-ray energy level.

In step (3) above, lattice planes appropriated for the energy level that was calculated in step (2) can be selected from the list of optimum lattice planes for various X-ray energy levels, shown in FIG. 12. In addition, when a normal tube type or a rotary type is to be used as the X-ray source 1, the kinds of constituent elements of the target object are preferably changed according to the X-ray energy level calculated in step (2). The changes are intended to utilize characteristic X-rays.

Since crystals are very susceptible to mechanical stresses, a crystal holder 16 for holding the analyzer crystal 4 is formed to have an L-shape so as to be able to securely support the crystal from two sides. Compared with the crystal 4, the X-ray source 1 is heavy, so the X-ray source is difficult to move for fine-adjustment. An angle of incidence of the X-ray 11 with respect to the analyzer crystal 4, therefore, is adjusted by moving the crystal 4. The analyzer crystal angle-adjusting unit 5 can use a normal swivel stage 17 for dρ control, and a θ-rotating stage 18. Rotation positioning accuracy of the rotating stage 18, however, needs to be narrowed down to a level low enough for the angular width that causes diffraction. A rotating stage (or the like) that uses a tangential bar whose accuracy is 100th of a second is suitable since the angular width that causes diffraction is usually several seconds of angle.

X-ray sensing pickup tubes, combinations of a phosphor, a lens system, and a CCD camera, or other equivalent units can be used as the image detectors 6 and 7.

Figure 13:
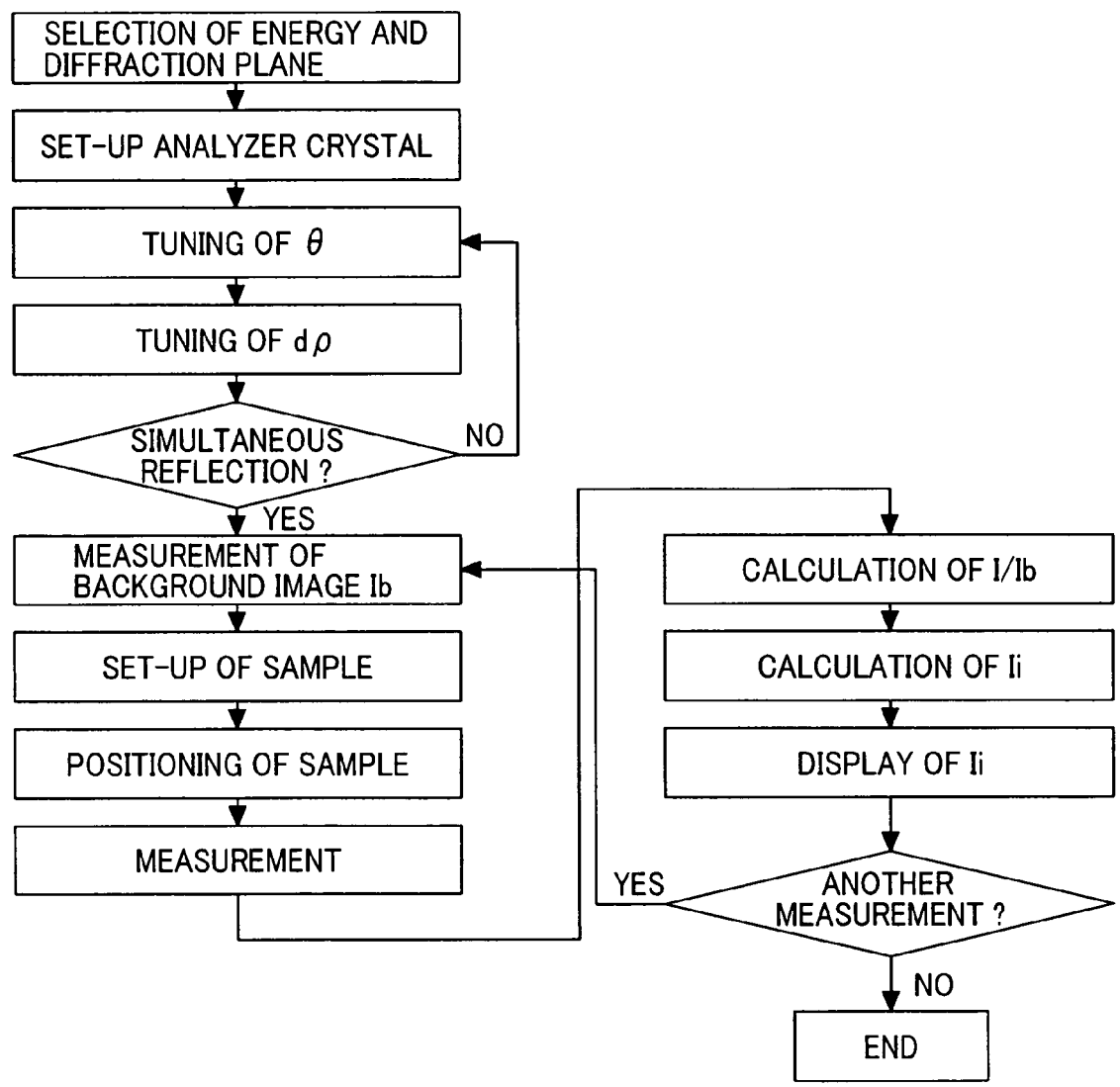
FIG. 13 is a diagram showing a measuring procedure to be used in the present invention.

A measuring procedure is flowcharted in FIG. 13. As described above, after an X-ray beam energy level and the diffraction lattice planes for simultaneous diffraction have been selected, an analyzer crystal 4 usable for the selected diffraction lattice planes is selected from a plurality of previously prepared analyzer crystals 4, and then the selected crystal 4 is secured to the analyzer crystal holder 16. Next, the selected analyzer crystal 4 is rotated by operating the θ-rotating stage 18 of the analyzer crystal angle-adjusting unit 5 to obtain a crystal angle at which the X-ray can be diffracted, that is, an angle $\theta_b$ that satisfies diffraction conditions. In this adjustment, if the analyzer crystal 4 has a secularly polished surface, the adjusting time required can be substantially reduced since adjustments that use X-rays can be performed easily after the angle has been adjusted to a range of several seconds using an auto-collimator 19 as shown in FIG. 10. The adjusting time can also be reduced if high-speed rotational scanning is possible by using PIN diode detectors, scintillation counters, or other rapid-response X-ray detectors, instead of the image detectors 6 and 7, during the angle adjustment. Next with the intensity levels of the diffracted X-ray beams 12 and 13 are being monitored, dρ axis rotation and θ-axis rotation are repeated in an alternate fashion to conduct adjustments for an angle at which the diffracted X-ray beams 12 and 13 appear at the same time. After the adjustments, background diffraction images are acquired using the image detectors 6 and 7, without the object 10 set up.

Next, the object 10 is set up in the object holder 2, then positioned using the object holder positioning unit 3, and measured. After a series of measurements with X-rays, image data that has been acquired with the object 10 set up is arithmetically subtracted the background image data in the processor 8, and then the "virtual diffraction intensity $I_i$ obtained in diffraction region C" is calculated using expression (11). Thus, an image with $I_i$ as contrast, namely, an image with a spatial differential of a phase shift as contrast, is obtained and then displayed at the display unit 14.

Figure 14A:
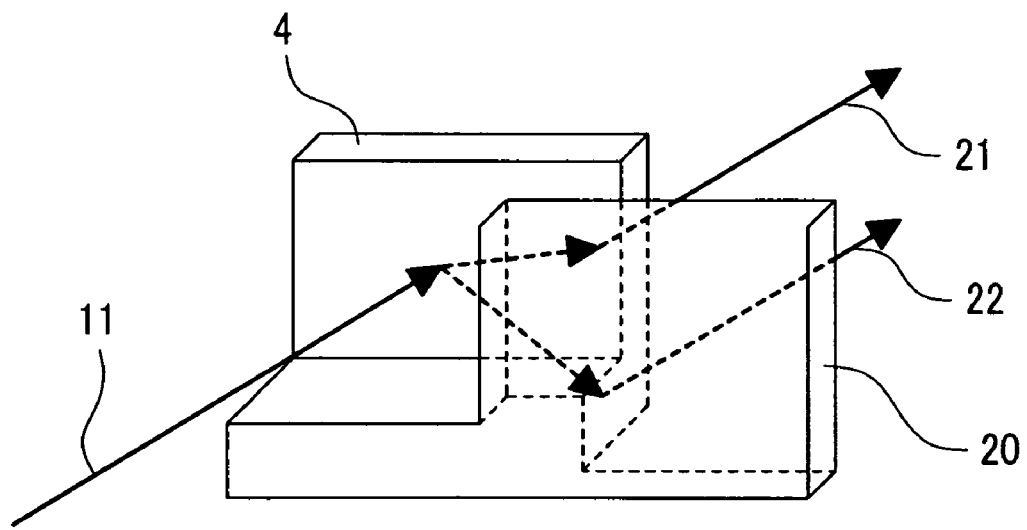
FIG. 14 is a structural diagram showing an analyzer crystal and a crystal plate.

In general, simultaneous diffraction is asymmetrical diffraction different in incident angle and exit angle, and appears with the object distorted on the diffraction images. In addition, as shown in FIG. 10, for the nonplanar type of simultaneous diffraction, the diffracted beams 12 and 13 exit obliquely with respect to the analyzer crystal 4, and thus the unit for positioning the image detectors 6 and 7 is required to be sophisticatedly movement. This problem can be solved by, as shown in FIG. 14A, providing at a downstream position of the analyzer crystal a crystal plate 20 whose plane is parallel a face opposed to the analyzer crystal 4. The X-ray beams that enter the crystal plate 20 are, needless to say, the beams 12 and 13 diffracted by the analyzer crystal.

Therefore, if the beam is diffracted on a lattice plane opposite a lattice plane of the crystal 4, that is, on the (n11) plane, the condition of diffraction on the (n−1−1) plane is satisfied automatically at the crystal plate 20. Similarly, if the beam is diffracted on the (n−1−1) plane, the condition of diffraction on the (n11) plane is satisfied automatically at the crystal plate 20. As shown in FIG. 14A, therefore, these beams are diffracted once again as X-ray beams 20 and 21 both parallel to the X-ray beam 11 that has transmitted the object. During the re-diffraction, since the diffraction is inverse asymmetrical diffraction with respect to the analyzer crystal 4, the distorted images of the object 10 are also corrected automatically. Although the analyzer crystal 4 and the crystal plate 20 can be independently constructed in terms of principles, if both are formed into an integrated crystal block as shown in FIG. 14A, the positioning and angle-adjusting units and other adjusting units can have respective configurations simplified, as is the case with the integration of the analyzer crystal into a single block.

Figure 14B:
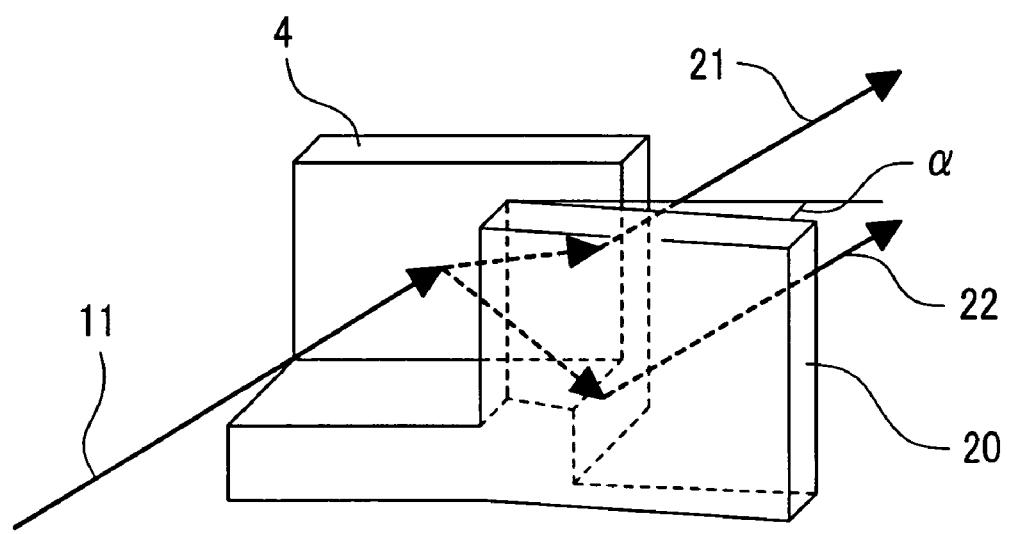

FIG. 14B shows a case in which the analyzer crystal 4 and the crystal plate 20 are non-parallel to each other and inclined by an angle α. In this case, X-ray beams 21 and 22 are spread by the crystal plate 20 at the same time the beams are diffracted thereby, so the object 10 can be observed with high spatial resolution. Image magnification ratio "b" is given by expression (17).

(Numerical expression 17)

$$b = \frac{\sin(\theta_i + \alpha)}{\sin(\theta_i - \alpha)} \quad (17)$$

In the above expression, α is an angle formed by the surfaces of the analyzer crystal 4 and the crystal plate 20. Since images are spread only in a $\theta_s$ direction and distorted, the distortion needs to be corrected by calculation in the processor when distortionless object images are required.

Figure 15A:
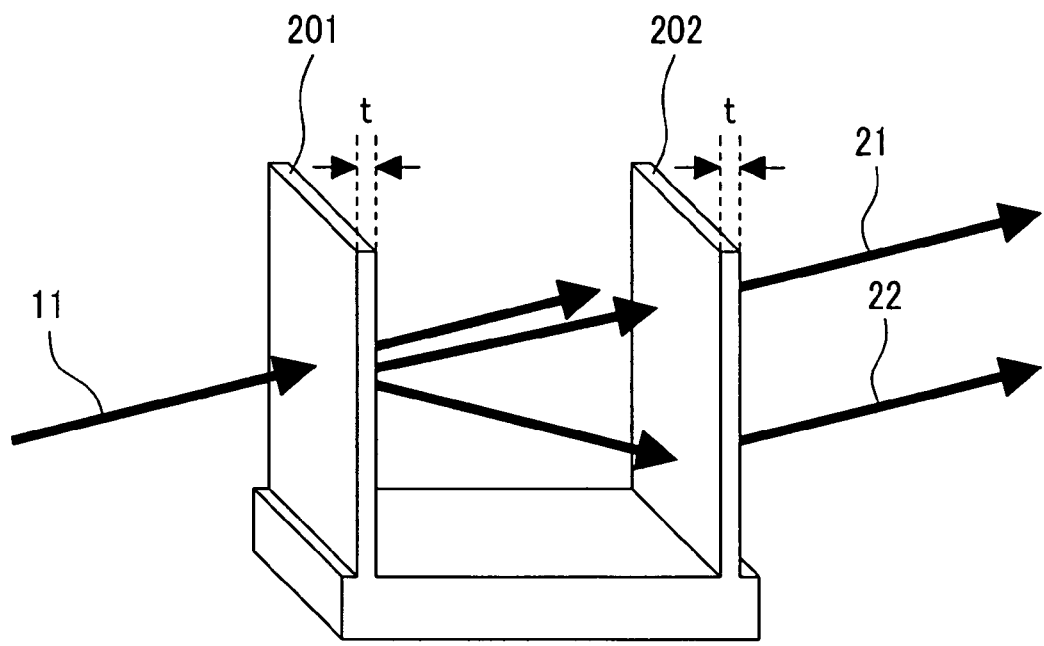
FIG. 15 is a structural diagram showing an analyzer crystal and crystal plate for Laue-case diffraction.
Figure 15B:
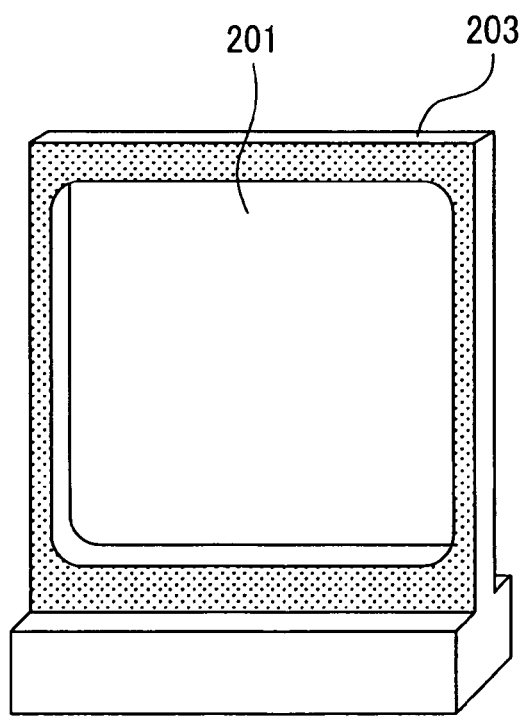

To extend an observation field, that is, $W_b$, the analyzer crystal 4 and the crystal plate 20 also need to be increased in size. For example, to obtain a 5-cm square observation field at an X-ray energy level of 15 keV for simultaneous diffraction on an Si (220) plane and an Si (202) plane, the analyzer crystal 4 needs to have very large sizes of at least 21 cm in width and at least 5 cm in height. To reduce crystal size, therefore, such Laue-case simultaneous diffraction as shown in FIG. 15A may be used instead of Bragg-case diffraction. In that case, crystal plates 201, 202 can be essentially of the same size as that of the observation field. Although thickness "t" of the crystal plates 201, 202 is desirably as thin as possible to avoid X-ray absorption, it is appropriate for "t" to be about 1 mm, since crystal plates that are too thin lose their mechanical rigidity as well and distort the crystals themselves. Even with the thickness of about 1 mm, however, absorption becomes too significant at low energy levels below 15 keV. In such a case, as shown in FIG. 15B, for example, the crystal plate 201 may be supported using a housing 203, and only a thickness of a crystal plate 201 through which an actual X-ray is to penetrate may be controlled below 1 mm. The same also applies to the crystal plate 202.

Figure 16:
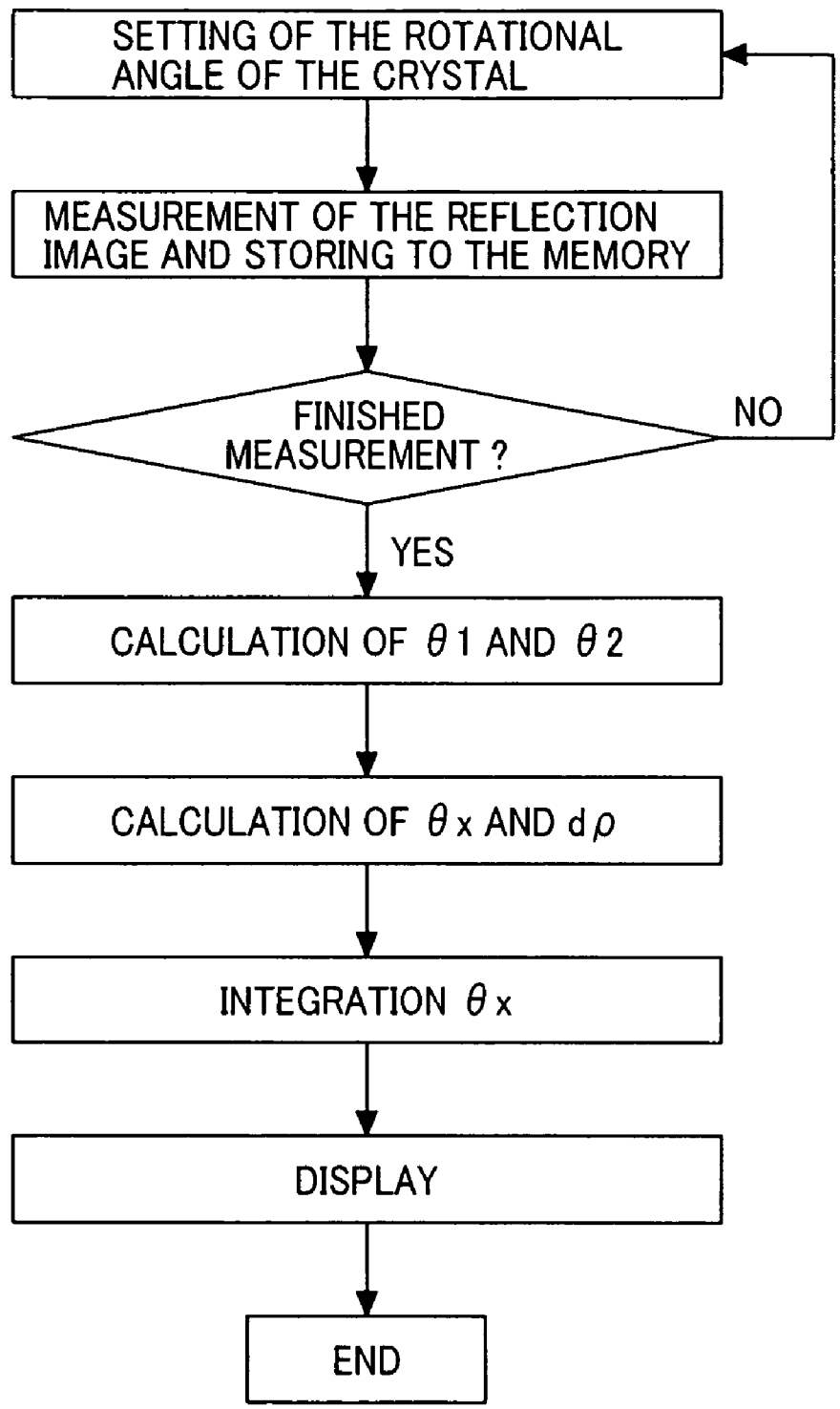
FIG. 16 is a diagram showing a procedure for measuring phase-contrast image data in the present invention.

A procedure for obtaining phase-contrast images of the object 10 is flowcharted in FIG. 16. These images can be obtained by measuring diffraction image data at various angles of the analyzer crystal 4, then after storing measured image data in the processor 8 and completing all measurements, activating the processor to calculate $\theta_1$ and $\theta_2$ at which diffraction intensity is maximized on a pixel-by-pixel basis, and calculating an integral of $\theta_x$ by deriving $\theta_x$ and dρ from $\theta_1$ and $\theta_2$, subject to expressions (12) and (13). In addition, if the X-ray source 1 is of the tube type or the like, since the X-ray beam 9 is a divergent beam of low parallelism, the phase shift of the background may incline and make it impossible to obtain accurate object images. If this is the case, pure phase-contrast images of the object 10 can be obtained by: before setting up the object 10, similarly to the above, executing the procedure of FIG. 16 to measure phase-shift image data to be used as the background; then setting up the object 10; and conducting subtractions from the images obtained by adding acquired object images and phase shifts of the background.

Figure 17:
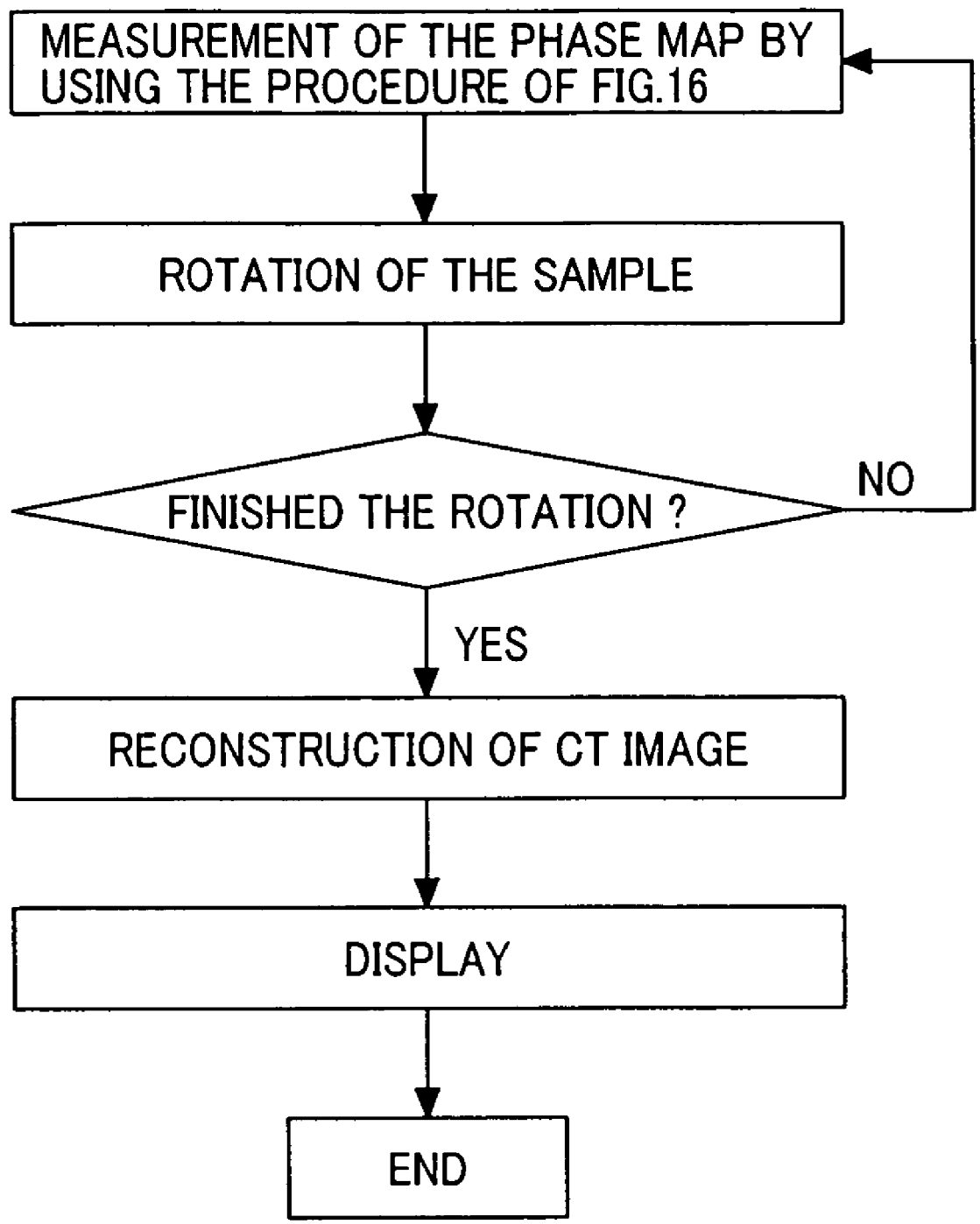
FIG. 17 is a diagram showing a procedure for measuring phase-contrast sectional image data in the present invention.

Sectional images of the object 10 can be obtained using the flowchart shown in FIG. 17, that is, by rotating the object 10 with respect to the X-ray beam 9, then obtaining phase-shift images at each rotational angle in accordance with the procedure of FIG. 16, and after conducting all measurements, activating the processor 8 to calculate sectional image data using a general X-ray CT algorithm. Any direction can be selected as a rotational axis of the object 10, provided that the axis is present in a plane vertical to the X-ray beam. Alternatively, the X-ray source 1, the analyzer crystal 4, and the detectors 6 and 7 may be rotated together around the object 10 after the object has been fixed.

Second Embodiment

Figure 18A:
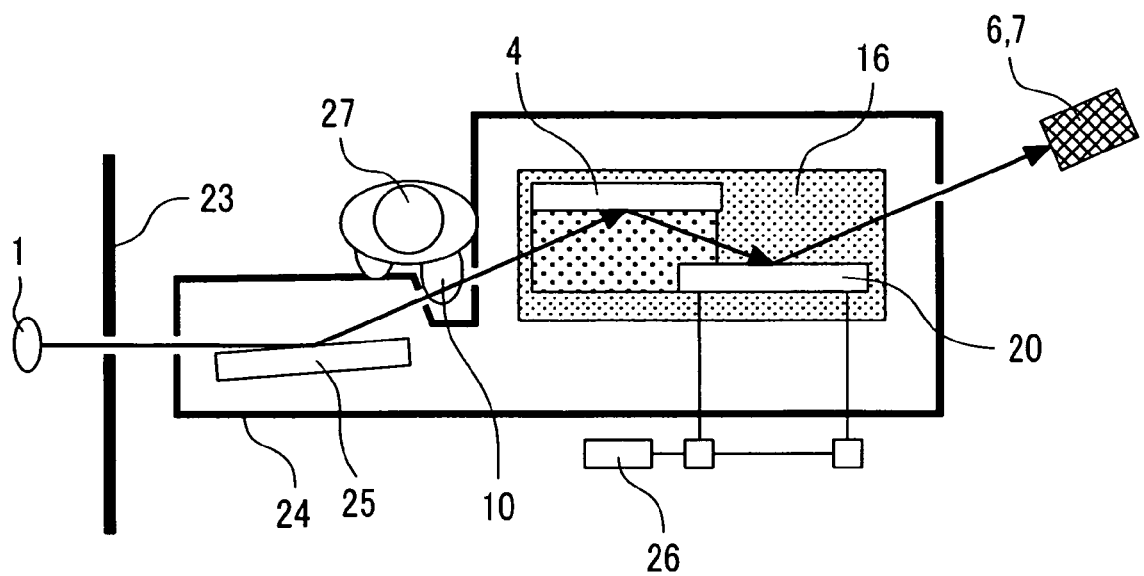
FIG. 18 is a diagram showing an embodiment of the present invention, applicable to a diagnosing system.
Figure 18B:
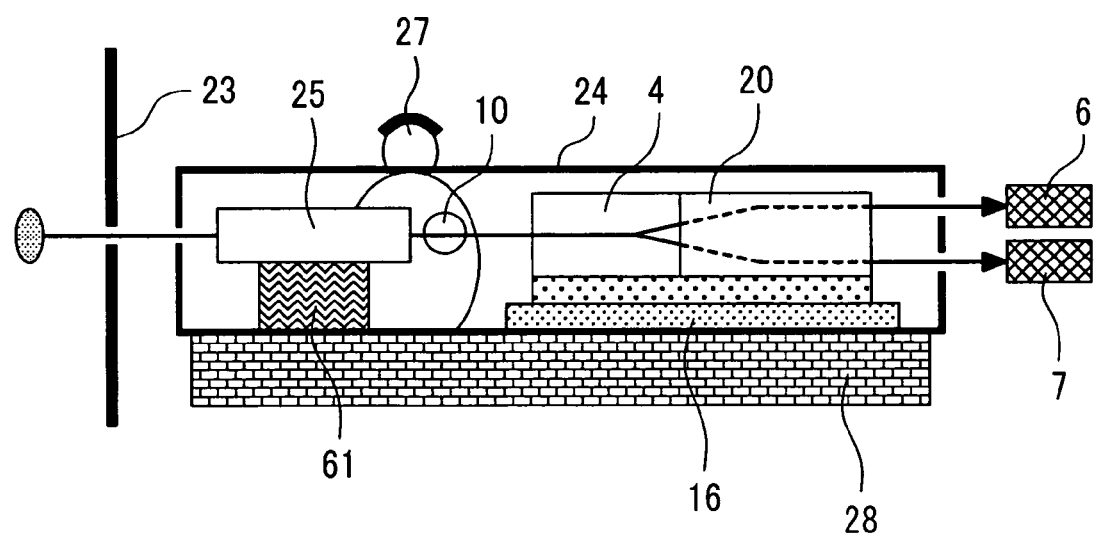

FIGS. 18A and 18B show a second embodiment of a mammography system (breast cancer diagnosing system) constructed as an example of a diagnosing system which utilizes such features of the imaging method of the present invention as very high sensitivity to light elements, and high suitability for observing biological soft tissues mainly composed of light elements. FIG. 18A is a top view schematically showing the above diagnosing system, and FIG. 18B is a side view schematically showing the diagnosing system. The diagnosing system is required to have a system component capable of minimizing an X-ray exposure rate, an observation field wide enough for the system to acquire a image of a target object at a time, and stability (reproducibility) high enough for the system to obtain the same image from any number of measurements repeated. In addition to the basic system configuration of the first embodiment, the second embodiment has an X-ray shield wall 23 for isolating an X-ray source 1 from a patient under examination, and an X-ray shield cover 24 for irradiating only a target object with X-rays. These added system components prevent X-ray irradiation of regions other than the patient's target regions to be X-ray irradiated. Both the X-ray shield wall 23 and the X-ray shield cover 24 have a small hole only at respective sections through which X-rays are passed. The system also has a beam-enlarging asymmetrical crystal plate 25 for shaping/enlarging an X-ray beam, and an angle feedback unit 26 for positioning an analyzer crystal 4 for an angle accuracy of 100th of a second. In addition, in order to avoid unnecessary image enlargement due to asymmetrical simultaneous diffraction at the analyzer crystal 4, and in order to ensure easy positioning of image detectors 6 and 7, the system employs the integrated structure shown in FIG. 14A, the structure being formed by integrating the analyzer crystal 4 and crystal plate 20 of FIG. 14A. The integrated structure is supported by a crystal holder 16. For reduced crystal size, however, the integrated structure may be used for such Laue-case diffraction as shown in FIG. 15A. The crystal holder 16 is controlled by a θ-rotating stage 18 as well as by the angle feedback unit 26. Specific structural examples of these system components will be described later herein. Reference number 61 denotes a supporting section of the beam-enlarging asymmetrical crystal plate 25. This supporting section, although not shown, has a diffraction angle controller.

The X-ray shield wall 23 is installed between the X-ray source 1 and the beam-enlarging asymmetrical crystal plate 25 in order to shield only unnecessary X-rays of all those emitted from the X-ray source 1. The X-ray shield wall 23 is a thick wall that contains lead and/or other substances, and this shield wall can shield 100% of X-ray intensity. The X-ray shield cover 24 is for totally covering the beam-enlarging asymmetrical crystal plate 25, the analyzer crystal 4, the crystal plate 20, and other major system components, and prevents the target object and the image detectors 6 and 7 from being irradiated with any X-rays scattered by each crystal. Since scattered X-rays are not too strong, a lead-containing acrylic plate, a thinly-lead-coated iron plate, or the like is used as the shield cover 24. The section thereof that is constructed to place the object 10 inside a path of the X-ray beam has a concave portion as shown in FIG. 18A. Patient except for the portion of the object 10 that is to be irradiated with the beam is thus protected therefrom.

Heat from a patient 27 under examination may cause undesirable events such as distortion of a lattice plane spacing between the beam-enlarging asymmetrical crystal plate 25 and the analyzer crystal 4. If the lattice plane spacing is likely to be disturbed for these reasons, the beam-enlarging asymmetrical crystal plate 25 and the analyzer crystal 4 are spaced at least 30 cm from each other to suppress the disturbance. Also, the floor vibration and/or other effects caused by a change of the patient 27 for another patient are suppressed by installing the beam-enlarging asymmetrical crystal plate 25, the analyzer crystal 4, and the crystal plate 20, on one vibration-insulating table 28. The vibration-insulating table 28 is also concave-shaped near the patient, preventing the patient from touching the table.

Figure 19:
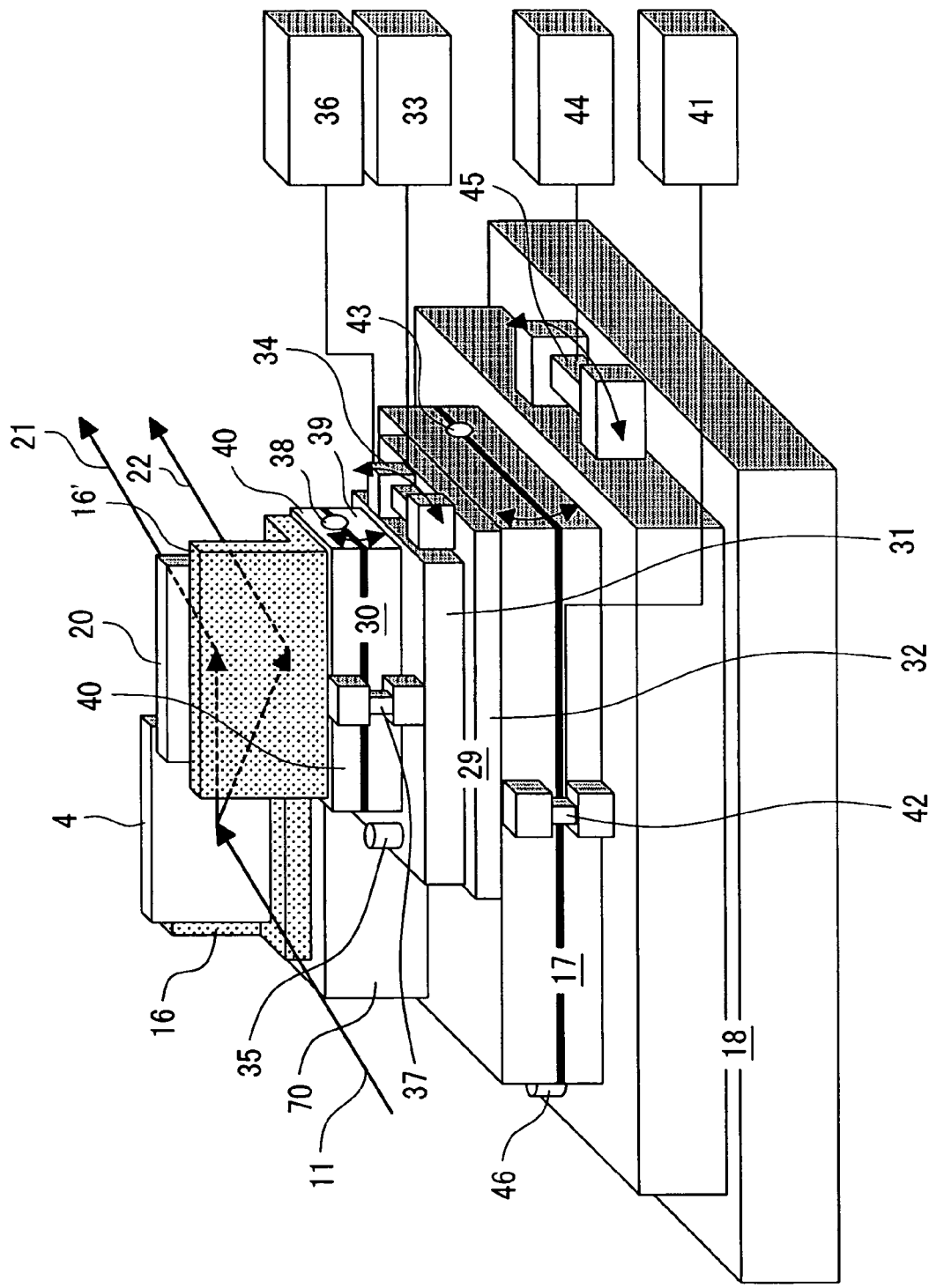
FIG. 19 is a detailed structural diagram showing an analyzer crystal and a crystal plate.

FIG. 19 is a diagram explaining more specifically a structural example relating to holding and controlling the analyzer crystal 4 and the crystal plate 20. Although the analyzer crystal 4 and the crystal plate 20 may be constructed into an integrated crystal block form as shown in FIG. 14, a size of this crystal block, that is, an observation field is most likely to be limited in that case. For a wider observation field, the analyzer crystal 4 and the crystal plate 20 are even more spaced for an isolated structure, and respective diffraction plane angles of the analyzer crystal 4 and the crystal plate 20 are controlled to essentially the same extent as that of the integrated formation thereof.

FIG. 19 assumes the above construction. That is to say, the analyzer crystal 4 and the crystal plate 20 are independently supported by the crystal holder 16 and a crystal holder 16', respectively, and independently placed on a table 70 and an upper table 40 of a second tilt stage 30, respectively. The additional intercrystal angle adjustment required by such separation of the analyzer crystal 4 and the crystal plate 20 is conducted using a second θ-stage 29 and the second tilt stage 30.

Figure 1:
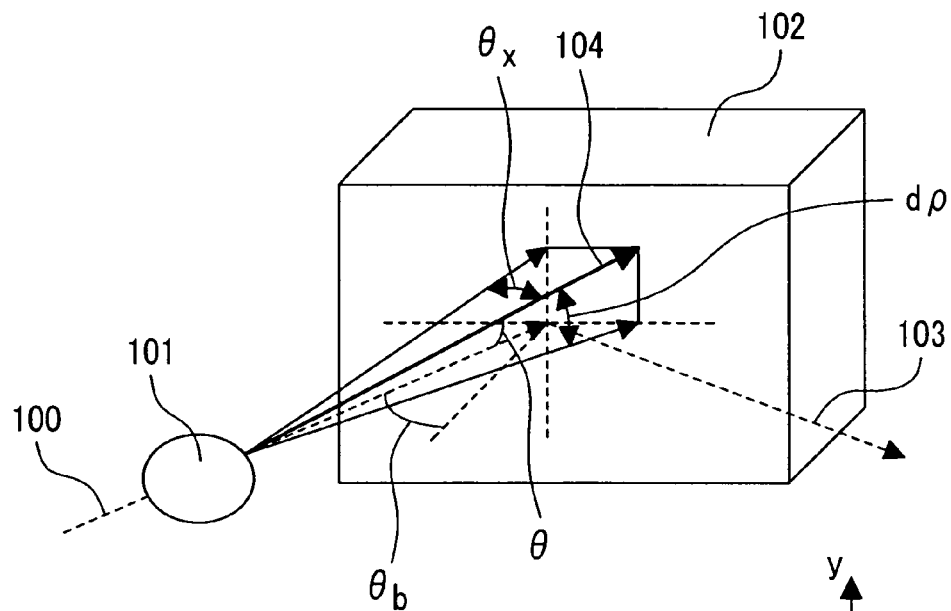
FIG. 1 is a diagram that shows two-dimensional X-ray refraction caused by a target object.
Figure 2:
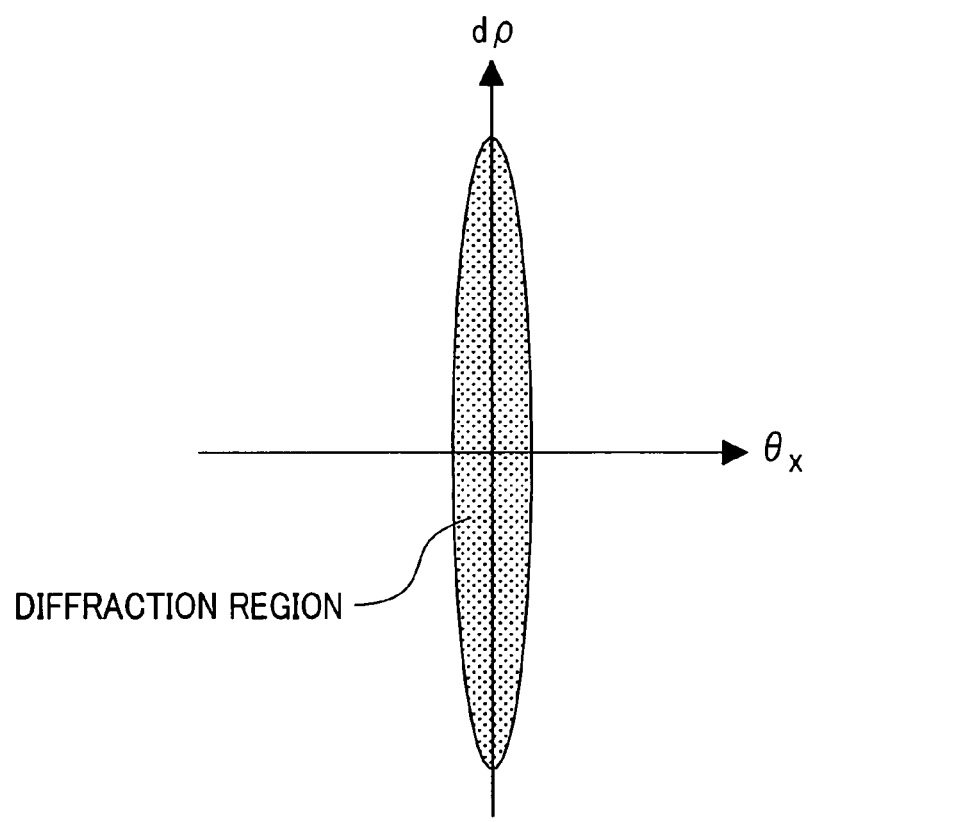
FIG. 2 is a diagram showing a region in which diffraction occurs for $\theta_x$ and $d\rho$.
Figure 4:
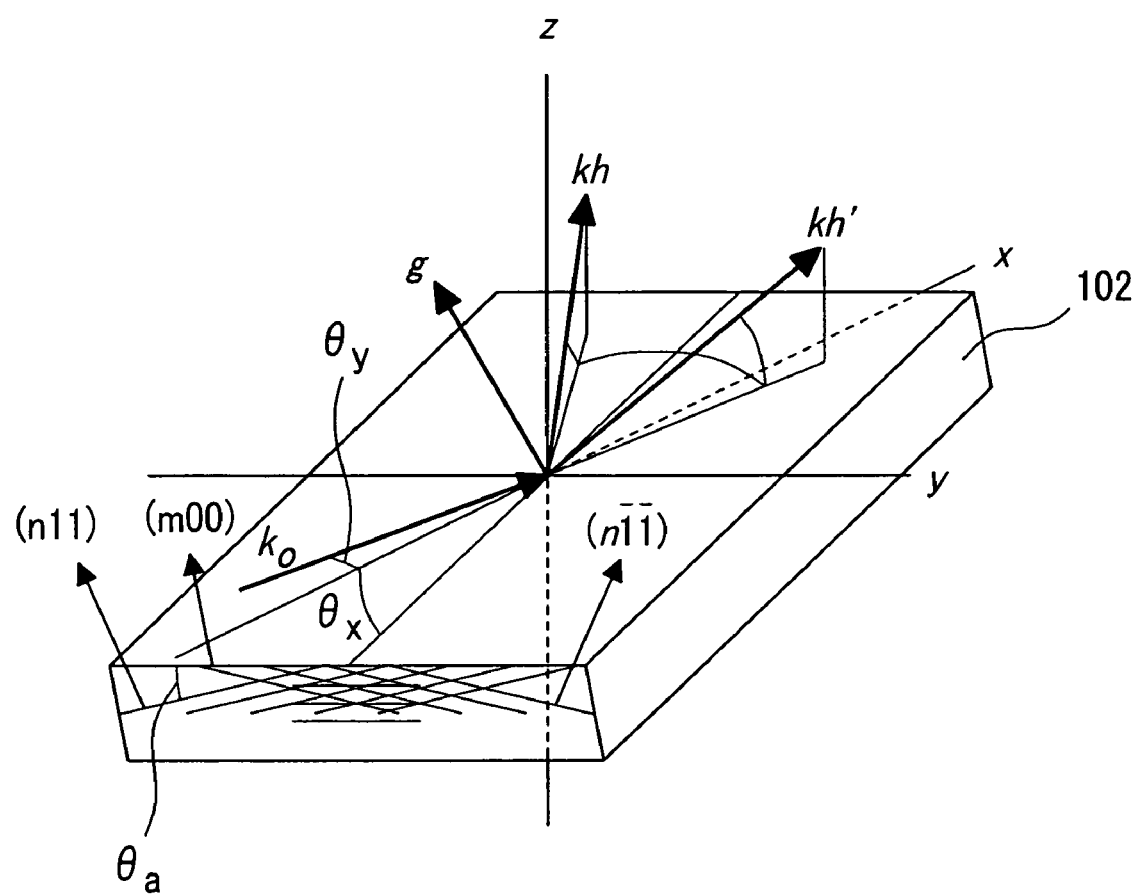
FIG. 4 is a diagram that shows simultaneous diffraction caused by crystals.
Figure 5:
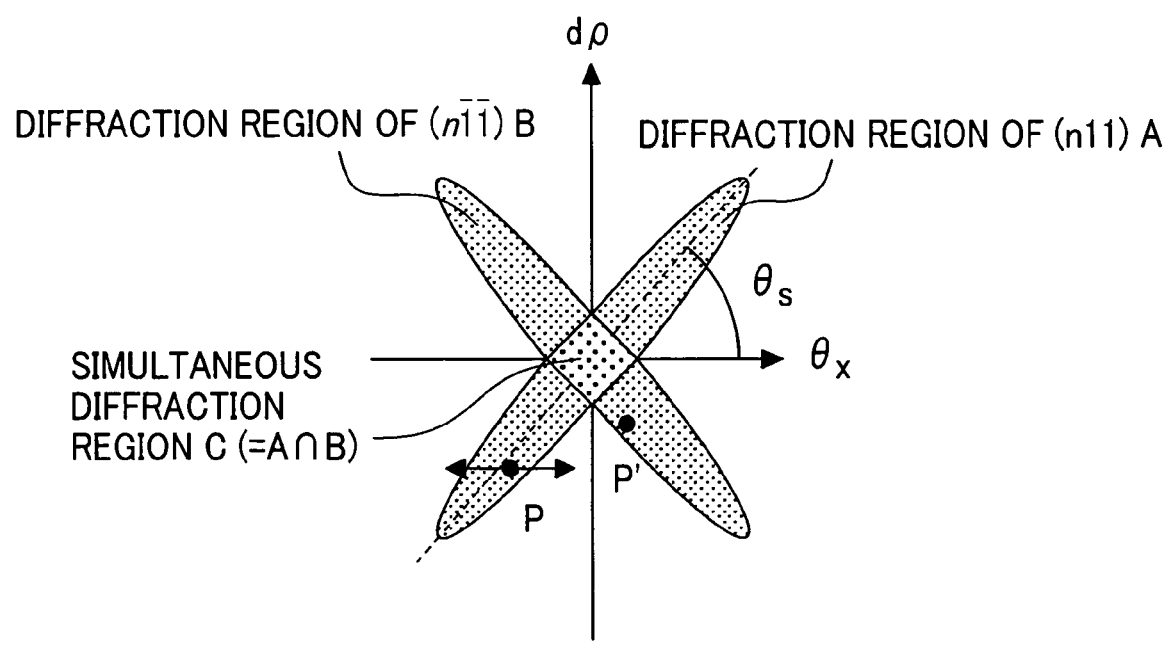
FIG. 5 is a diagram that shows regions in which diffraction occurs for $\theta_x$ and $d\rho$ of simultaneous diffraction.
Figure 7:
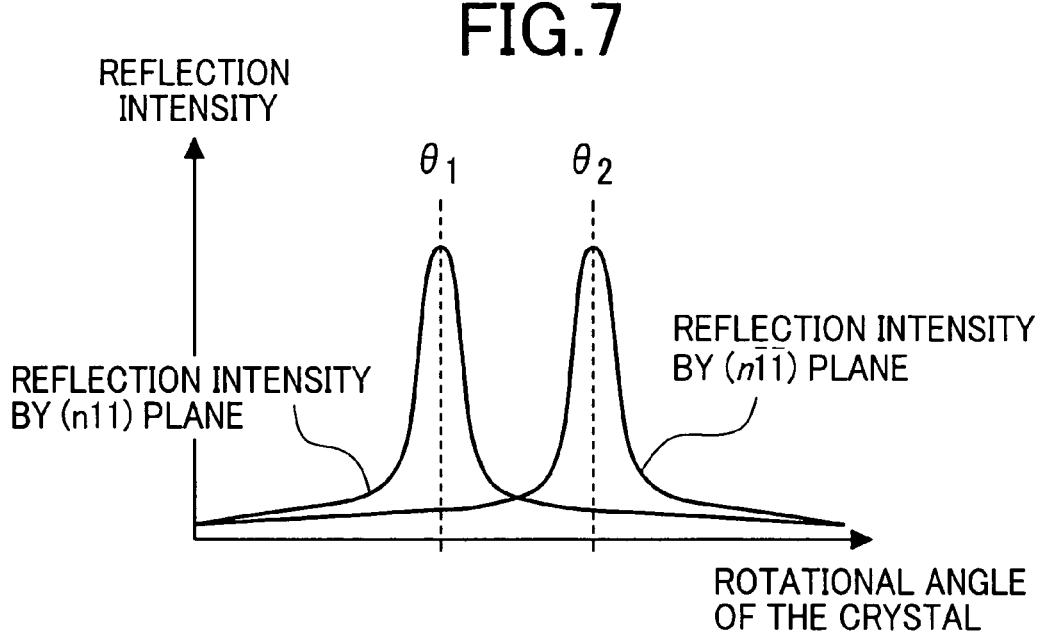
FIG. 7 is a diagram that shows changes in diffraction intensity due to $\theta_x$ rotation.
Figure 8:
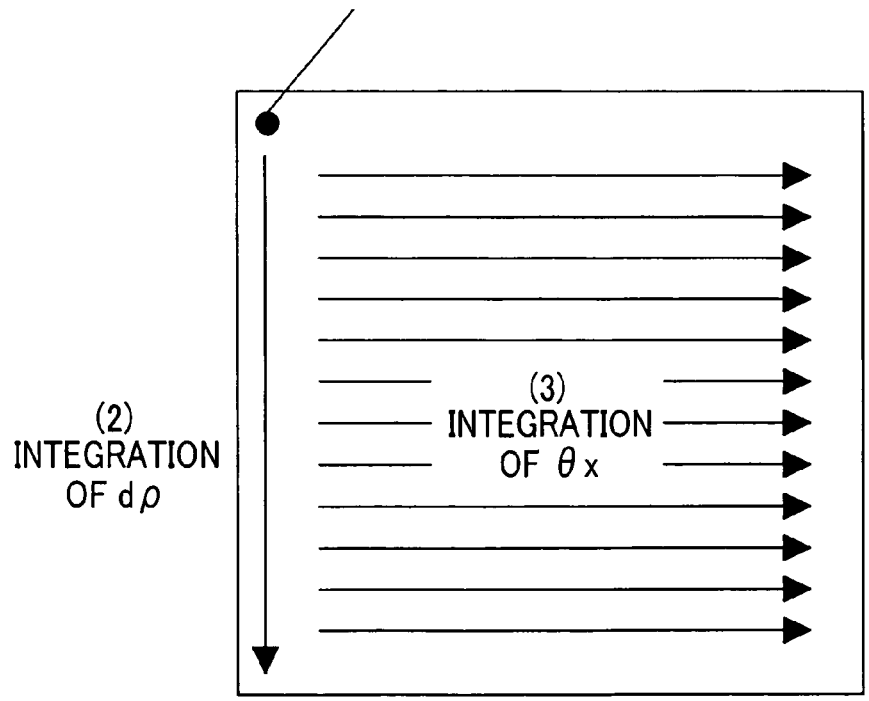
FIG. 8 is a diagram showing an integration procedure to be used during integral calculation of a phase shift.

To ensure an observation field sizes of 10 cm×10 cm, each crystal needs to have a length of at least 50 cm for an X-ray energy level of 35 keV. For this reason, the second θ-stage 29 uses a solid-state sleeve bearing capable of obtaining high mechanical rigidity, even for increased crystal sizes. That is, as shown, an upper table 31 of the second θ-stage 29 is mounted on a lower table 32 via a solid-state sleeve member made of a specially processed synthetic resin. Also, the upper table is connected at its left end to the lower table by a pivot 35. In addition, an expandable unit that uses a piezoelectric element 34 is provided at a right end of the upper table. The expandable unit using the piezoelectric element 34 is fixed at one end to the upper table 31 and at the other end to the lower table 32. When a control voltage source 33 is changed in output voltage and the piezoelectric element 34 is expanded/contracted, therefore, the upper table 31 is driven to rotate around the pivot 35, in a direction of the arrow shown at right of the second θ-stage 29. An area of a section at which the upper table 31 and the lower table 32 are in contact with each other via the sleeve member is larger than for a normal stage using ball bearing, so that high mechanical rigidity is obtainable. The rotation of the upper table 31 with respect to the lower table 32 rotates the second tilt stage 30 supported on the upper table 31, thus causing the crystal plate 20 supported on the second tilt stage 30 to rotate with the crystal holder 16'. The respective diffraction plane angles of the analyzer crystal 4 and the crystal plate 20 can thus be rotated about the y-axis shown in FIG. 4.

Also, the second tilt stage 30 has an upper table 40 and a lower table 39 connected to each other at one end by a roll bearing 38, and has an expandable unit that uses a piezo-electric element 37, at an edge of the other end. The expandable unit using the piezoelectric element 37 is fixed at one end to the upper table 40 and at the other end to the lower table 39. When a control voltage source 36 is changed in output voltage and the piezoelectric element 37 is expanded/contracted, therefore, the upper table 40 is driven to rotate around the roll bearing 38, in a direction of the arrow shown at right of the second tilt stage 30. The rotation of the upper table 40 causes the crystal plate 20 supported thereon to rotate with the crystal holder 16'. The respective diffraction plane angles of the analyzer crystal 4 and the crystal plate 20 can thus be rotated about the x-axis shown in FIG. 4.

Since the table 39 and the table 40 are in contact with each other linearly via the roll bearing 38, mechanical rigidity decreases in comparison with that of the solid-state sleeve bearing of the second θ-stage 29. Even so, it is possible to obtain higher rigidity than for a normal stage using ball bearing.

In addition, a tilt stage 17 on which the analyzer crystal 4, the crystal plate 20, the second θ-stage 29, and the second tilt stage 30 are mounted is of the same structure as that of a second θ-tilt stage 30. The tilt stage 17 has upper and lower tables connected to each other at one end by a roll bearing 43, and has an expandable unit that uses a piezoelectric element 42, at an edge of the other end. When a control voltage source 41 is changed in output voltage and the piezoelectric element 42 is expanded/contracted, the tilt stage 17 is driven to rotate around the roll bearing 43. A θ-stage 18 with the tilt stage 17 thereon is of the same structure as that of the second θ-stage 29. The θ-stage 18 has upper and lower tables connected to each other at one end by a pivot 46, and has an expandable unit that uses a piezo-electric element 45, at an edge of the other end. When a control voltage source 44 is changed in output voltage and the piezoelectric element 45 is expanded/contracted, the θ-stage 18 is driven to rotate around pivot 46.

Figure 20:
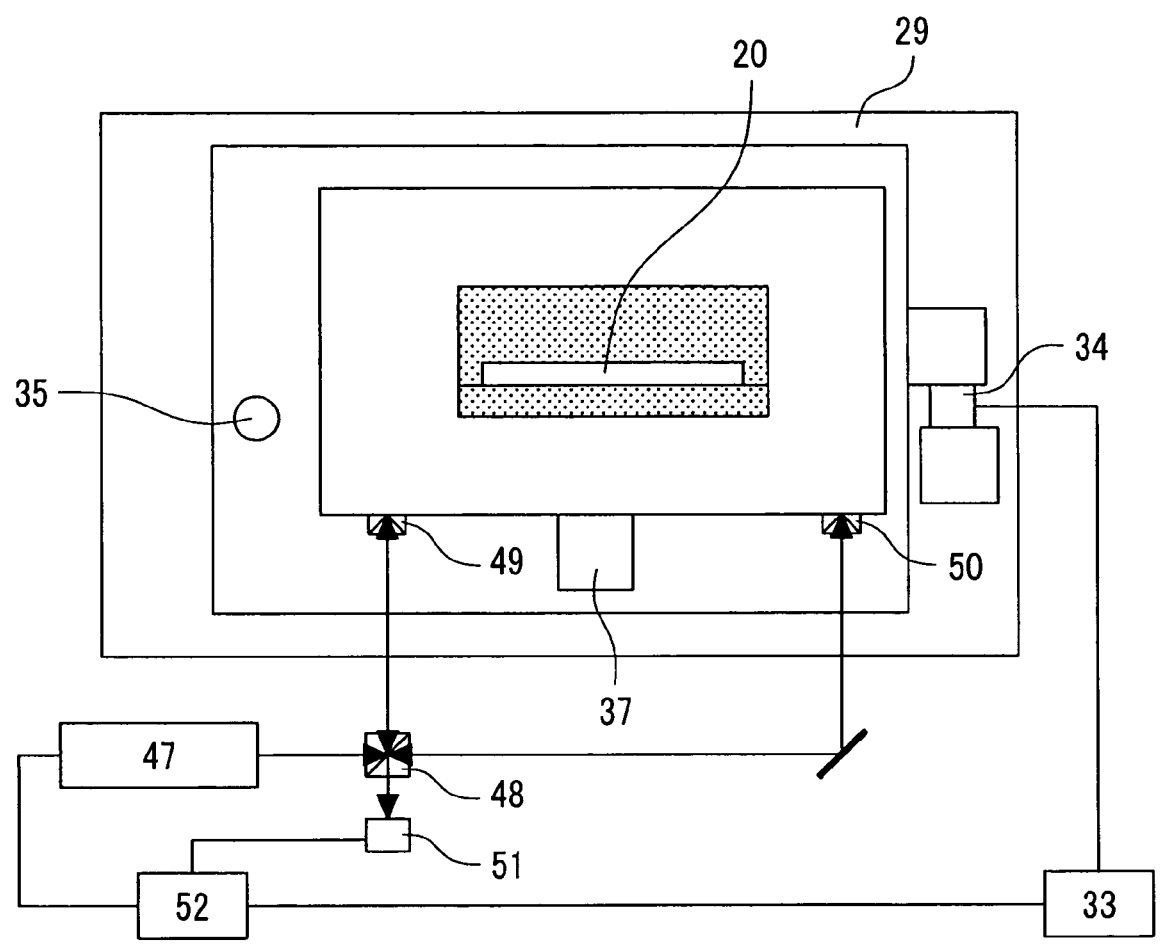
FIG. 20 is a diagram showing a construction of a feedback unit.

To achieve high measuring repeatability, rotational drifts of each stage need to be controlled below 100th of a second of angle. Such an angle feedback unit as shown in FIG. 20 is therefore provided. Only a feedback unit of the second θ-stage 29 is shown in FIG. 20. For other axes, rotational drifts can also be suppressed by incorporating a similar feedback unit. This feedback unit is adapted to measure each crystal angle using a laser-based optical method, then after calculating a deviation ΔA with respect to a preset angle, use the control voltage source 33 to adjust according to ΔA, the voltage applied to the piezoelectric element 34, and control ΔA to zero. For angle detection, a laser beam emitted from a laser 47 is split into two beams by a half-mirror 48, then these beams are diffracted by table-mounted corner cubes 49 and 50, and the diffracted beams are coupled, and made to interfere with each other via the half-mirror 48. Intensity of the interference is monitored by a detector 51, and a signal from the laser is processed/calculated by a processor 52, whereby an angle is detected. The laser light may be diffracted on the crystal surface itself, not on the corner cubes.

During breast cancer diagnosis, the thickness (breast) of the target object significantly varies from person to person. Therefore, thicknesses of individual target objects are measured beforehand, then as described in the first embodiment, optimum X-ray energy is determined using such a graph as in FIG. 11, and lattice planes to be used for simultaneous diffraction are further determined in accordance with FIG. 12. At this time, crystals that have Si (422) crystal surfaces are convenient since any combination, whether it be a combination of Si (220) and Si (202), Si (440) and Si (404), or Si (660) and Si (606), can be immediately used only by adjusting angle without replacing the analyzer crystal.

As described in the first embodiment, measurements with X-rays are conducted using the flowchart of FIG. 13 to obtain images whose spatial differentials of phase shifts are to be taken as contrast, or using the flowchart of FIG. 16 to obtain images whose phase shifts are to be taken as contrast. However, compared with the former method, the latter method increases a dose rate, so the former method may be used for a screening examination, and the latter method for a re-examination and a closer examination.

The explanation used in the drawings of the invention is as follows:

1 . . . X-ray source, 2 . . . Target object holder, 3 . . . Object holder retaining/positioning unit, 4 . . . Analyzer crystal, 5 . . . Analyzer crystal angle-adjusting unit, 6 . . . Image detector, 7 . . . Image detector, 8 . . . Processor, 9 . . . X-ray beam, 10 . . . Target object, 11 . . . X-ray beam, 12 . . . Diffracted X-ray beam, 13 . . . Diffracted X-ray beam, 14 . . . Display unit, 15 . . . Slit, 16 . . . Crystal holder, 17 . . . Swivel stage, 18 . . . θ-rotating stage, 19 . . . Auto-collimator, 20 . . . Crystal plate, 21 . . . Diffracted X-ray beam, 22 . . . Diffracted X-ray beam, 23 . . . X-ray shield wall, 24 . . . X-ray shield cover, 25 . . . Beam-enlarging asymmetrical crystal plate, 26 . . . Angle feedback unit, 27 . . . Patient under examination, 28 . . . Vibration-insulating table, 29 . . . Second θ-stage, 30 . . . Second tilt stage, 31 . . . Table, 32 . . . Table, 33 . . . Control voltage source, 34 . . . Piezoelectric element, 35 . . . Pivot, 36 . . . Control voltage source, 37 . . . Piezoelectric element, 38 . . . Roll bearing, 39 . . . Table, 40 . . . Table, 41 . . . Control voltage source, 42 . . . Piezoelectric element, 43 . . . Roll bearing, 44 . . . Control voltage source, 45 . . . Piezoelectric element, 46 . . . Pivot, 47 . . . Laser, 48 . . . Half-mirror, 49 . . . Corner cube, 50 . . . Corner cube, 51 . . . Detector, 52 . . . Processor, 201 . . . Crystal plate, 202 . . . Crystal plate, 203 . . . Housing.

What is claimed is:

1. An X-ray imaging system, comprising:
   means for irradiating a target object with an X-ray beam;
   an analyzer crystal splitting a transmitting X-ray beam of the object into a plurality of diffracted beams non-parallel to one another by simultaneous X-ray diffraction;
   a plurality of X-ray detectors which each detect a corresponding one of the diffracted X-ray beams; and
   a processor which arithmetically processes a plurality of signals output from the plurality of X-ray detectors;
   wherein:
   the analyzer crystal rotates with respect to the transmitting X-ray beam; and
   the processor obtains an image, in which a spatial differential of the phase shift and the phase shift of the transmitting X-ray beam caused by the object are both taken as contrast, using the plurality of diffracted X-ray beams that each the X-ray detectors detect at each rotational angle of the analyzer crystal.

2. The X-ray imaging system according to claim 1, wherein information of each crystal angle position at which an intensity of each diffracted beam becomes a maximum is used for arithmetic processing conducted to obtain an image of the object.

3. The X-ray imaging system according to claim 2, further comprising a function that rotates the object with respect to the transmitting X-ray beam, wherein a sectional image that takes a phase shift of the transmitting X-ray beam caused by the object as contrast, is obtained using images which take the phase shifts of the object obtained at each rotational angle as contrast.

4. The X-ray imaging system according to claim 1, further comprising a function that rotates the object with respect to the transmitting X-ray beam, wherein a sectional image that takes a phase shift of the transmitting X-ray beam caused by the object as contrast, is obtained using images which take the phase shifts of the object obtained at each rotational angle as contrast.

5. The X-ray imaging system according to claim 1, wherein a combination of an energy level of the X-ray beam and X-ray simultaneous diffraction lattice planes is either 7-15 keV and Si (202), Si (220), 15-30 keV and Si (404), Si (440), or at least 30 keV and Si (606), Si (660).

6. An X-ray imaging system, comprising:
   an X-ray source;
   means for shaping/enlarging a beam emitted from the X-ray source;
   means for setting up a target object on an optical path of the shaped/enlarged beam;
   means for preventing X-ray irradiation into a region outside of a beam irradiation region of the object;
   an analyzer crystal which splits the transmitting X-ray beam of the object into a first X-ray beam and a second X-ray beam non-parallel to each other by simultaneous X-ray diffraction;
   an exit crystal which diffracts the first X-ray beam and the second X-ray beam into a third X-ray beam and a fourth X-ray beam, respectively, both the third X-ray beam and the fourth X-ray beam being roughly parallel to the transmitting X-ray beam;
   an X-ray detector that detects the third X-ray beam and the fourth X-ray beam;
   a processor which arithmetically obtains an image in which a spatial differential of the phase shift of the transmitting X-ray beam caused by the object is taken as contrast using a signal output from the X-ray detector; and a function which rotates the analyzer crystal and the exit crystal together with respect to the transmitting X-ray beam, wherein an image, in which a spatial differential of the phase shift and the phase shift itself of the transmitting X-ray beam caused by the object are taken as contrast, is arithmetically obtained using intensity of the third X-ray beam and fourth X-ray beam detected by the X-ray detector at each rotational angle.

7. The X-ray imaging system according to claim 6, wherein the rotating function includes a feedback mechanism to suppress drift rotation of the analyzer crystal and the exit crystal and has an angular positioning repeatability of hundredths of a second.

8. The X-ray imaging system according to claim 7, further comprising a function which rotates the object with respect to the transmitting X-ray beam, wherein a sectional image that takes a phase shift of the transmitting X-ray beam caused by the object as contrast, is obtained using images which take the phase shifts of the object obtained at each rotational angle.

9. The X-ray imaging system according to claim 6, wherein information of each crystal angle position at which the intensity of the third X-ray beam and the fourth X-ray beam each become a maximum is used for arithmetic processing conducted to obtain an image of the object.

10. The X-ray imaging system according to claim 9, further comprising a function which rotates the object with respect to the transmitting X-ray beam, wherein a sectional image that takes a phase shift of the transmitting X-ray beam caused by the object as contrast, is obtained using images which take the phase shifts of the object obtained at each rotational angle.

11. The X-ray imaging system according to claim 6, further comprising a function which rotates the object with respect to the transmitting X-ray beam, wherein a sectional image that takes a phase shift of the transmitting X-ray beam caused by the object as contrast, is obtained using images which take the phase shifts the object obtained at each rotational angle.

12. The X-ray imaging system according to claim 6, wherein a combination of an energy level of the X-ray beam and X-ray simultaneous diffraction lattice planes is either 7-15 keV and Si (202), Si (220), 15-30 keV and Si (404), Si (440), or at least 30 keV and Si (606), Si (660).

13. The X-ray imaging system according to claim 6, wherein respective X-ray beam incident sides of the analyzer crystal and the exit crystal differ from exit sides of the diffracted X-ray beams formed by the simultaneous X-ray diffraction.

14. An X-ray imaging system comprising:
an X-ray source:
means for shaping/enlarging a beam emitted from the X-ray source;
means for setting up a target object on an optical path of the shaped/enlarged beam;
means for preventing X-ray irradiation into a region outside of a beam irradiation region of the object;
an analyzer crystal which splits the transmitting X-ray beam of the object into a first X-ray beam and a second X-ray beam non-parallel to each other by simultaneous X-ray diffraction;

an exit crystal which diffracts the first X-ray beam and the second X-ray beam into a third X-ray beam and a fourth X-ray beam, respectively, both the third X-ray beam and the fourth X-ray beam being roughly parallel to the transmitting X-ray beam;

an X-ray detector that detects the third X-ray beam and the fourth X-ray beam;

a processor which arithmetically obtains an image in which a spatial differential of the phase shift of the transmitting X-ray beam caused by the object is taken as contrast using a signal output from the X-ray detector; and a function which rotates the analyzer crystal and the exit crystal together with respect to the transmitting X-ray beam, wherein an image, in which a spatial differential of the phase shift and the phase shift itself of the transmitting X-ray beam caused by the object are taken as contrast, is arithmetically obtained using intensity of the third X-ray beam and fourth X-ray beam detected by the X-ray detector at each rotational angle, wherein respective X-ray beam incident sides of the analyzer crystal and the exit crystal differ from exit sides of the diffracted X-ray beams formed by the simultaneous X-ray diffraction.

15. The X-ray imaging system according to claim 14, wherein the rotating function includes a feedback mechanism to suppress drift rotation of the analyzer crystal and the exit crystal and has an angular positioning repeatability of hundredths of a second.

16. The X-ray imaging system according to claim 15, further comprising a function which rotates the object with respect to the transmitting X-ray beam, wherein a sectional image that takes a phase shift of the transmitting X-ray beam caused by the object as contrast, is obtained using images which take the phase shifts of the object obtained at each rotational angle.

17. The X-ray imaging system according to claim 14, wherein information of each crystal angle position at which the intensity of the third X-ray beam and the fourth X-ray beam each become a maximum is used for arithmetic processing conducted to obtain an image of the object.

18. The X-ray imaging system according to claim 17, further comprising a function which rotates the object with respect to the transmitting X-ray beam, wherein a sectional image that takes a phase shift of the transmitting X-ray beam caused by the object as contrast, is obtained using images which take the phase shifts of the object obtained at each rotational angle.

19. The X-ray imaging system according to claim 14, further comprising a function which rotates the object with respect to the transmitting X-ray beam, wherein a sectional image that takes a phase shift of the transmitting X-ray beam caused by the object as contrast, is obtained using images which take the phase shifts the object obtained at each rotational angle.

* * * * *